United States Patent [19]

Kahn et al.

[11] Patent Number: 4,860,759
[45] Date of Patent: Aug. 29, 1989

[54] VITAL SIGNS MONITOR

[75] Inventors: Alan R. Kahn; Jennifer K. Chandler, both of Cincinnati, Ohio

[73] Assignee: Criticare Systems, Inc., Waukesha, Wis.

[21] Appl. No.: 93,952

[22] Filed: Sep. 8, 1987

[51] Int. Cl.$^4$ .............................................. A61B 5/02
[52] U.S. Cl. .................................... 128/668; 128/706; 128/700
[58] Field of Search ............................... 128/632–634, 128/664, 665, 668, 670, 696, 700, 706

[56] References Cited

U.S. PATENT DOCUMENTS

| | | | |
|---|---|---|---|
| 3,548,806 | 12/1970 | Fisher | 128/2.05 |
| 4,154,231 | 5/1979 | Russell | 128/700 |
| 4,232,682 | 11/1980 | Veth | 128/671 |
| 4,379,460 | 4/1983 | Judell | 128/671 |
| 4,422,458 | 12/1983 | Kravath | 128/671 |
| 4,495,950 | 1/1985 | Schneider | 128/670 |
| 4,517,986 | 5/1985 | Bilgutay | 128/671 |
| 4,519,396 | 5/1985 | Epstein et al. | 128/698 |
| 4,548,204 | 10/1985 | Groch et al. | 128/700 |
| 4,669,485 | 6/1987 | Russell | 128/679 |
| 4,676,252 | 6/1987 | Trautman et al. | 128/671 |

OTHER PUBLICATIONS

"Operating Manual for ML-105 Arterial Tonometer", Aug. 1977, Nicolet Instrument Corporation, p. 401, Section 4.02.
"A Microprocessor-Based Arterial Tonometer", by Dennis E. Bahr, Member, IEEE; Krishan K. Dhupar, Member, IEEE; Jeffrey C. Petzke and Erich T. Ziemann, Nicolet Instrument Corporation, pp. 90–98, 1978.
"Indirect Measurement of Instantaneous Arterial Blood Pressure in the Human Finger by the Vascular Unloading Technique", by Ken-Ichi Yamakoshi, Hideaki Shimazu and Tatsuo Togawa, 1980, IEEE, pp. 150–155.
"The VFA Method for Non-Invasive Analysis of Left Ventricular Function", by Kahn, A.; Baharestani, H.; Dh-par, K.; Bahr, D., Oct. 6–10, 1979, p. 78, Section 9.7.
"A Nonauscultatory Method for Systolic and Diastolic Pressure", by L. A. Geddes and S. J. Whistler, Oct. 21–25, 1978, pp. 120, Section 14.6.
"Arrival Time and Calibrated Contour of the Pulse Wave, Determined Indirectly from Recordings of Arterial Compression Sounds", by Simon Rodbard, M.D. Ph.D., Herbert M. Rubinstein, M.D., and Sol Rosenblum, M.D., Buffalo, N.Y., pp. 205–212, American Heart Journal, vol. 53, 1957.
"Measurement of Pulsatile Blood Flow Velocity in Microvessels from Single Photometric Detector", by John Silva and Marcos Intaglietta, IEEE Transactions on Biomedical Engineering, Jul. 1973.

Primary Examiner—Max Hindenburg
Assistant Examiner—Randy Citrin
Attorney, Agent, or Firm—Willian Brinks Olds Hofer Gilson & Lione

[57] ABSTRACT

A vital signs monitor includes an ECG sensor, an oximetric finger probe, a respiration impedance sensor, a respiration strain gauge, and a blood pressure cuff with a pressure sensor. Signals generated by these sensors are processed by a microcomputer which is programmed to cross-reference data from multiple channels in order to improve accuracy. The microcomputer is programmed to select the more regular pulses from the ECG sensor and the finger probe to arrive at a better measure of heart rate. In addition, the microcomputer is programmed to use the strain gauge signal to remove artifacts from the signal generated by the impedance sensor. In this way a more artifact-free measure of respiration rate is obtained. Blood pressure is measured by using timing information derived from pulses sensed by the oximetric finger probe in combination with signals generated by the blood pressure cuff pressure sensor to determine systolic and diastolic pressures of the subject. A calibrated blood pressure waveform is generated automatically from the oximetric finger probe and the blood pressure cuff.

4 Claims, 19 Drawing Sheets

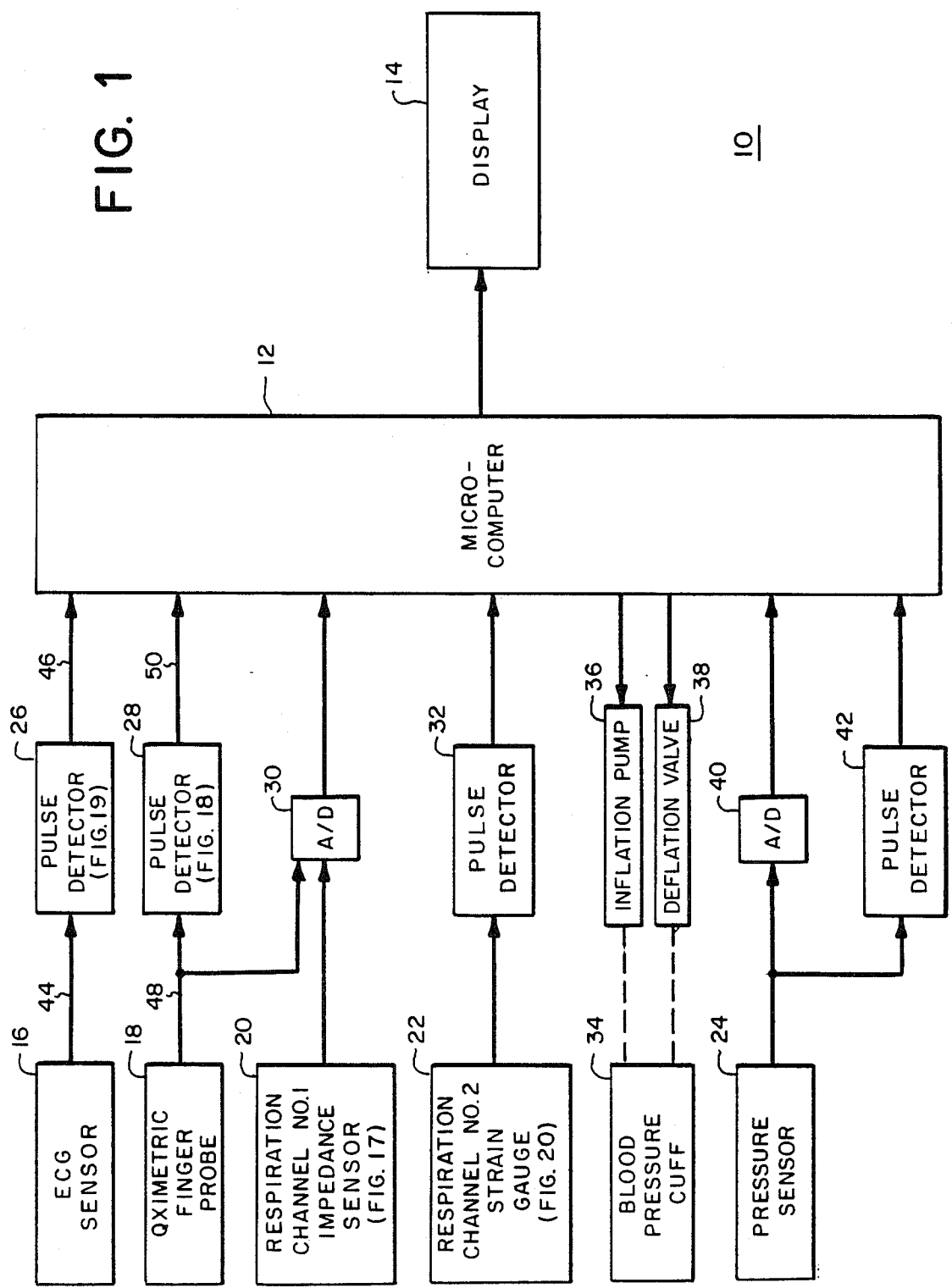

ECG WAVEFORM

ECG WAVEFORM

FINGER PROBE WAVEFORM

FINGER PROBE WAVEFORM

ECG PULSES

ECG PULSES

RESPIRATION-IMPEDANCE (a)

TIME ⟶

STRAIN GAUGES-RESPIRATION ARTIFACTS (b)

NORMAL BREATHING    COUGH    NORMAL BREATHING    COUGH

ONE-SHOT
PULSE DETECTION
TO MICROPROCESSOR

ONE-SHOT
PULSE DETECTION
TO MICROPROCESSOR

WAVEFORM TO A/D
OR PULSE DETECTION
TO MICROPROCESSOR

VITAL SIGNS MONITOR

BACKGROUND OF THE INVENTION

This invention relates to a vital signs monitor which combines the signals from multiple sensors to generate more reliable measurements of vital signs such as heart rate, respiration rate, and vasomotor activity.

Conventional vital signs monitors use single sensors to measure individual vital signs. For example, an ECG sensor can be used to measure heart rate, or a chest strap connected to a strain gauge can be used to measure respiration rate. Such single sensor techniques are prone to measurement errors when the sensor generates artifacts as a result of body motion, poor sensor placement, and the like. At least in part for this reason, vital signal monitors are often restricted to use by highly trained personnel, as for example in an intensive care unit.

There is a need for a vital signs monitor which is less dependent on the error-free operation of individual sensors. Such a monitor could be used effectively by less highly trained personnel, and would be better suited for use by a subject at home, without the assistance of a health care professional.

SUMMARY OF THE INVENTION

The vital signs monitor of this invention combines information from multiple sensors to improve the reliability and the accuracy with which vital signs are measured. It has been found that the signals generated by sensors commonly used in vital sign monitors can be cross-referenced to reduce measuring errors and increase accuracy, without significantly increasing the cost or the electronic complexity of the monitor.

For example, an ECG sensor can be used to generate a first series of pulses indicative of heart rate, but chest motion of the subject may interfere with the ECG sensor. Similarly, an oximetric finger probe can be used to generate a second series of pulses indicative of heart rate, but hand motion of the subject may interfere with the finger probe signal. The monitor described below responds to both the first and second pulses by identifying those pulses with more regularly repeating pulse intervals and by using the identified pulses to determine heart rate of the subject. In this way, proper operation continues, even when the ECG signal or the finger probe signal is interrupted.

As another example, a conventional electrical impedance sensor can be attached to the chest of a subject to generate a series of impedance pulses correlated with respiration rate. However, chest motion such as that associated with a cough will often create additional impedance pulses which can result in an over estimate of respiration rate. The monitor described below suppresses these additional impedance pulses by using a chest wall motion sensor (such as a chest strap coupled to a mechanical strain gauge) to detect chest motion artifacts. Impedance pulses associated with such chest motion artifacts are then suppressed.

As a third example, vasomotor activity can be monitored by automatically comparing core blood pressure with the waveform generated by an oximetric finger probe. The ratio of pulse amplitude as measured with an occluding cuff over a major artery to pulse amplitude of the finger probe waveform is an excellent measure of the extent to which the vascular bed at the finger is dilated or constricted. As described below, this ratio can be automatically measured and checked for trends that may give advance warnings of impending changes in core blood pressure.

In each of these three examples, two separate sensor signals are correlated to generate an accurate measure of the desired parameter. The heart rate measurement approach described above is relatively undemanding with respect to sensor placement, since either of the two sensors can supply information to the monitor if the other fails to provide a reliable signal. The respiration rate measuring approach is relatively immune to chest motion artifacts since the chest wall motion sensor provides an excellent indication of such artifacts. The vasomotor activity monitoring approach provides an accurate measure of dilation and constriction of a peripheral vascular bed.

The invention itself, together with further objects and attendant advantages, will best be understood by reference to the following detailed description, taken in conjunction with the accompanying drawings.

DETAILED DESCRIPTION OF THE PRESENTLY PREFERRED EMBODIMENTS

Figure 16A:
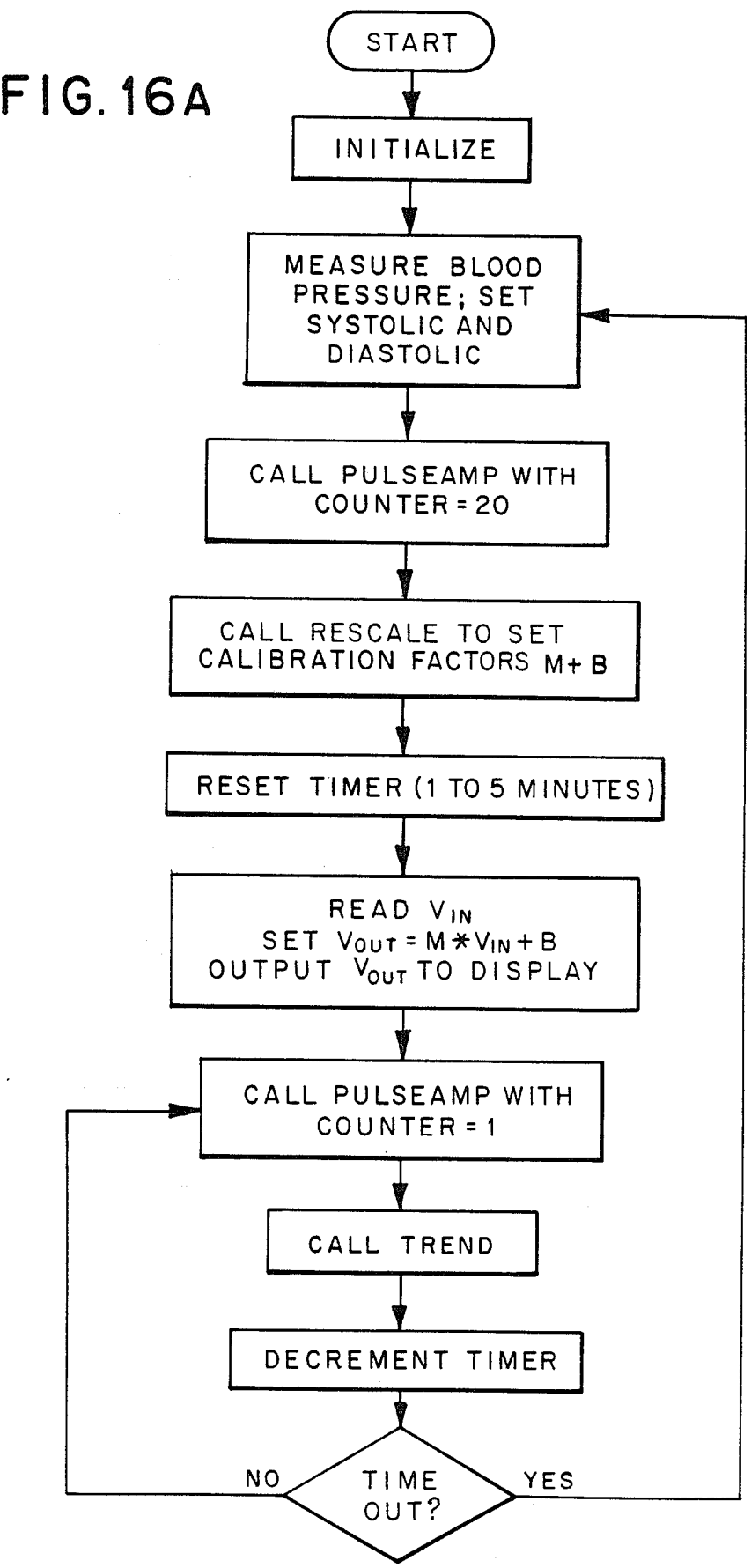
FIGS. 16a-16e are flow charts of the vasomotor activity detection and blood pressure waveform display system of the monitor of FIG. 1.
Figures 1, 16B:
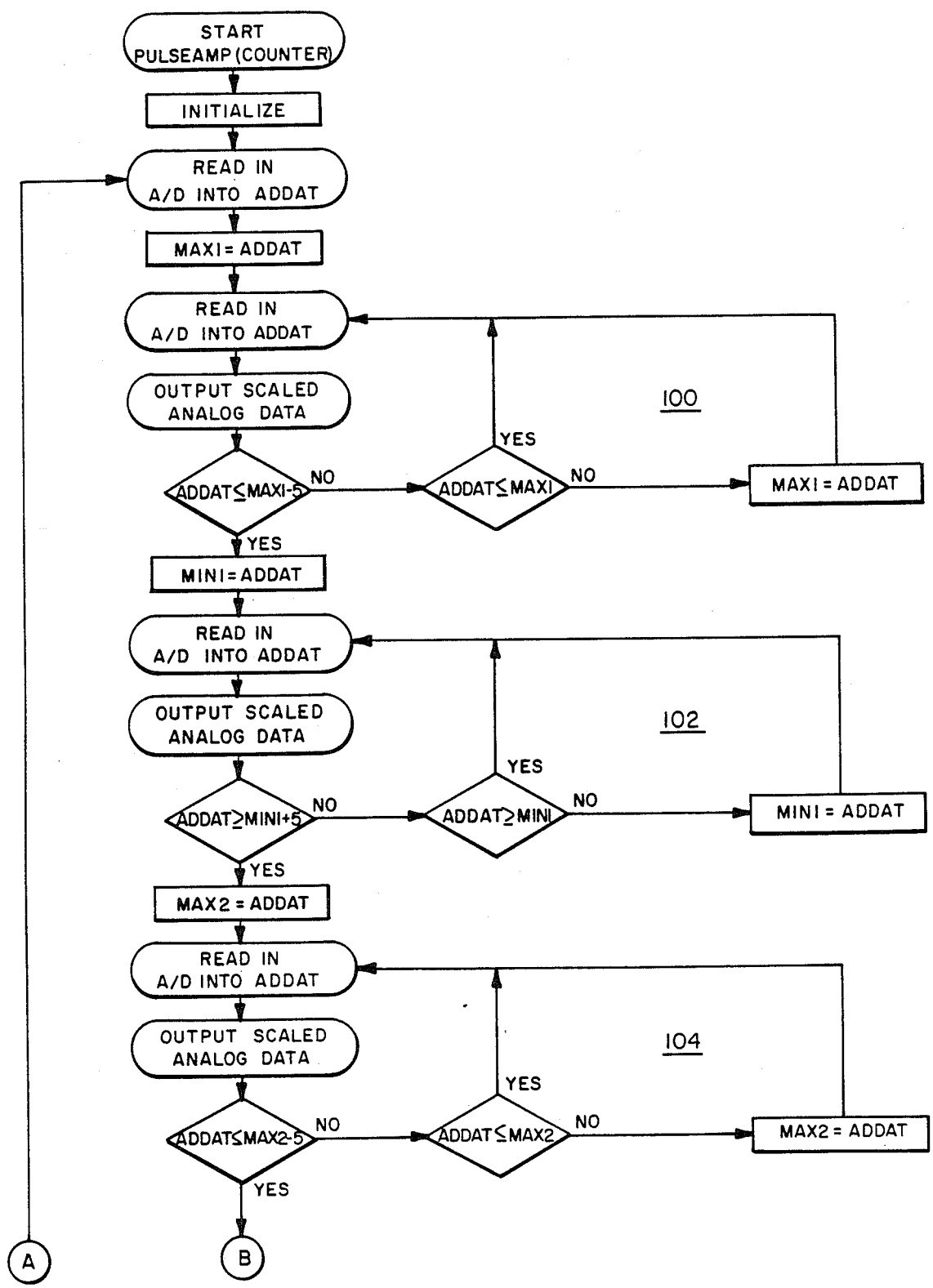
FIG. 1 is a block diagram of a vital signs monitor which incorporates the presently preferred embodiments of this invention.
Figures 2, 16B:
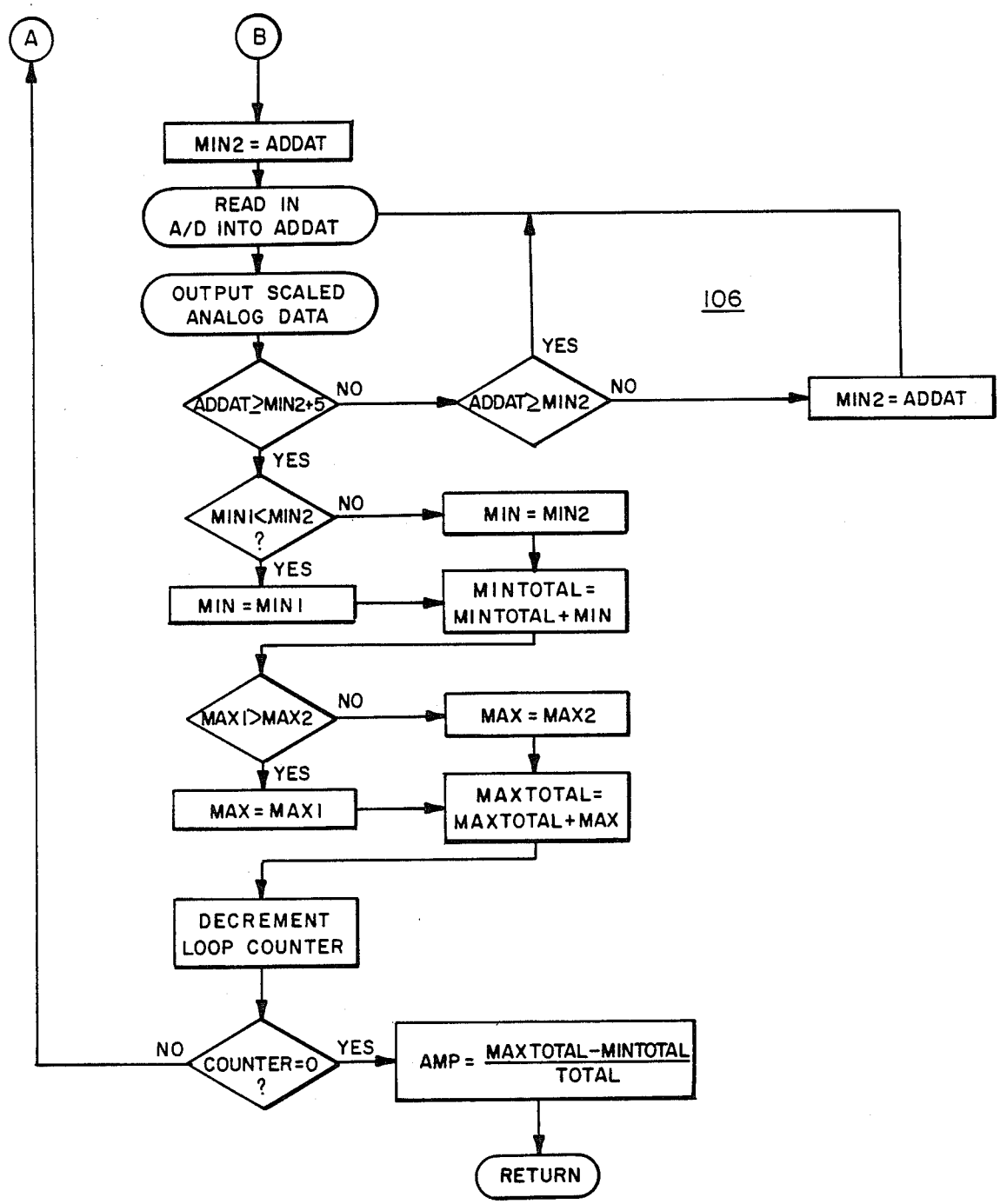

Turning now to the drawings, FIG. 1 shows a block diagram of a vital signs monitor 10 that incorporates presently preferred embodiments of this invention. This monitor 10 includes a microcomputer 12 which controls a display 14. A number of sensors, including an ECG sensor 16, an oximetric finger probe 18, an impedance sensor 20, a strain gauge 22, and a blood pressure cuff pressure sensor 24, generate waveforms. These waveforms, after suitable signal processing, are interrelated as described below by the microcomputer 12 in order to generate reliable measures of heart rate, respiration rate, and blood pressure.

The ECG sensor 16 is a conventional system used to monitor electrical voltages associated with cardiac activity. The waveforms generated by the ECG sensor 16 are processed in a pulse detector 26 to generate a train of ECG pulses which are applied as signal inputs to the microcomputer 12.

The oximetric finger probe 18 is a conventional sensor which optically monitors the transmission or reflection of light through the finger of the subject to generate a periodic signal. The AC component of this periodic signal can be used as a measure of pulse rate of the subject. The periodic signal generated by the oximetric finger probe 18 is applied to a pulse detector 28, which generates a series of finger probe pulses applied as inputs to the microcomputer 12.

Sensors such as the electrical impedance sensor 20 of FIG. 1 are conventionally attached to the chest of a subject to provide a measure of respiration. Rhythmic chest motion associated with breathing results in an AC component of the signal generated by the sensor 20. This signal is digitized in an A/D converter 30, and the digitized signal (including the periodic component) is applied as an input to the microcomputer 12.

Similarly, chest straps are conventionally used to monitor respiration, and such chest straps typically contain strain gauges such as the strain gauges 22 of FIG. 1. The strain gauges 22 generate a waveform having a low amplitude periodic component correlated with the periodic chest motion of breathing and high amplitude peaks associated with artifacts such as coughing. This signal waveform is applied to a pulse detector 32 which is selectively responsive only to large peaks to generate pulses which are applied as an input to the microcomputer 12. Pulse detector 32 responds only to large pulses, and therefore the output of the pulse detector 32 is indicative of artifacts.

As shown in FIG. 1 the monitor 10 also includes a blood pressure cuff 34. This cuff 34 is of the conventional type which is intended to be wrapped around the upper arm of the subject so as selectively to block blood flow through the arm. The cuff 34 is inflated by an inflation pump 36 controlled by the microcomputer 12, and the cuff 34 is deflated by a deflation valve 38 also controlled by the microcomputer 12. The pressure sensor 24 monitors the air pressure within the blood pressure cuff 34, and produces a pressure signal which is digitized in an A/D converter 40 and applied as an input to the microcomputer 12. In addition, the pressure signal generated by the pressure sensor 24 is applied to a pulse detector 42, which generates a series of pulses that are also applied as an input to the microcomputer 12.

Figure 17:
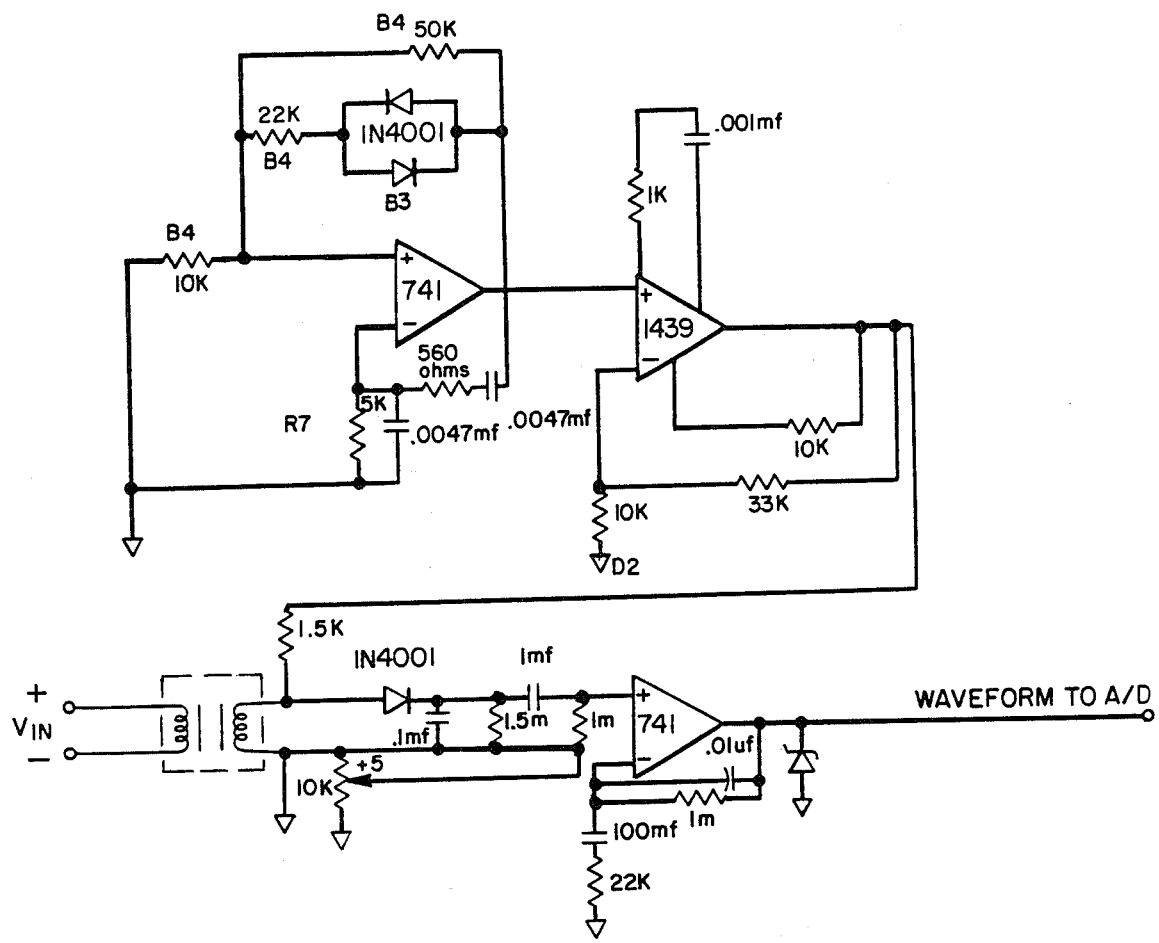
FIGS. 17-20 are detailed schematic diagrams of electronic circuits suitable for use in the monitor of FIG. 1.
Figure 18:
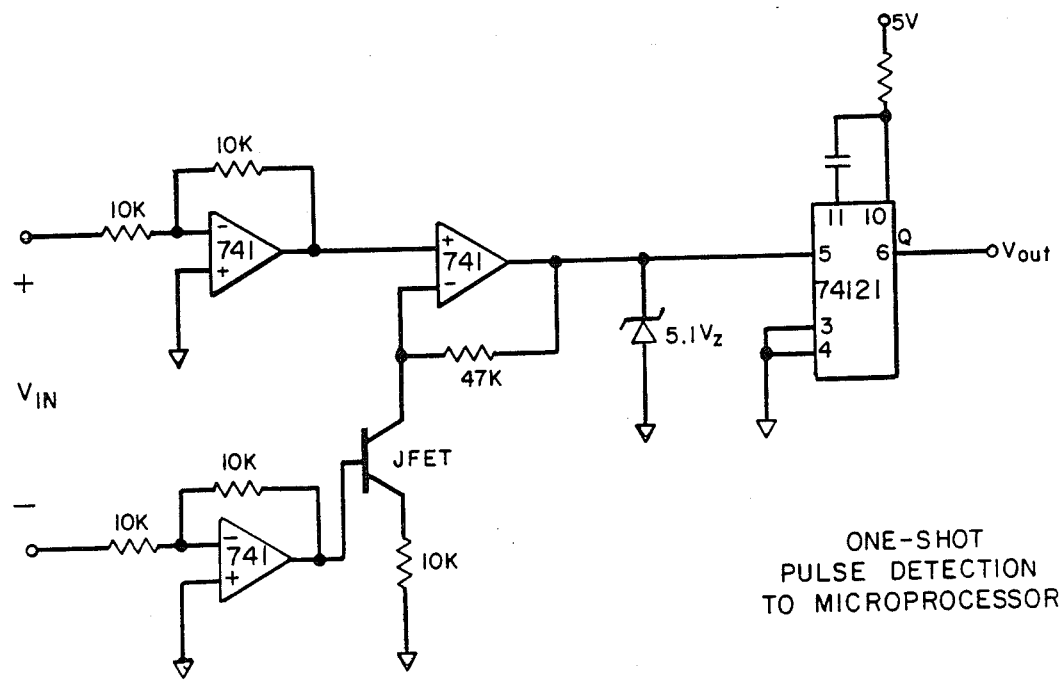
Figure 19:
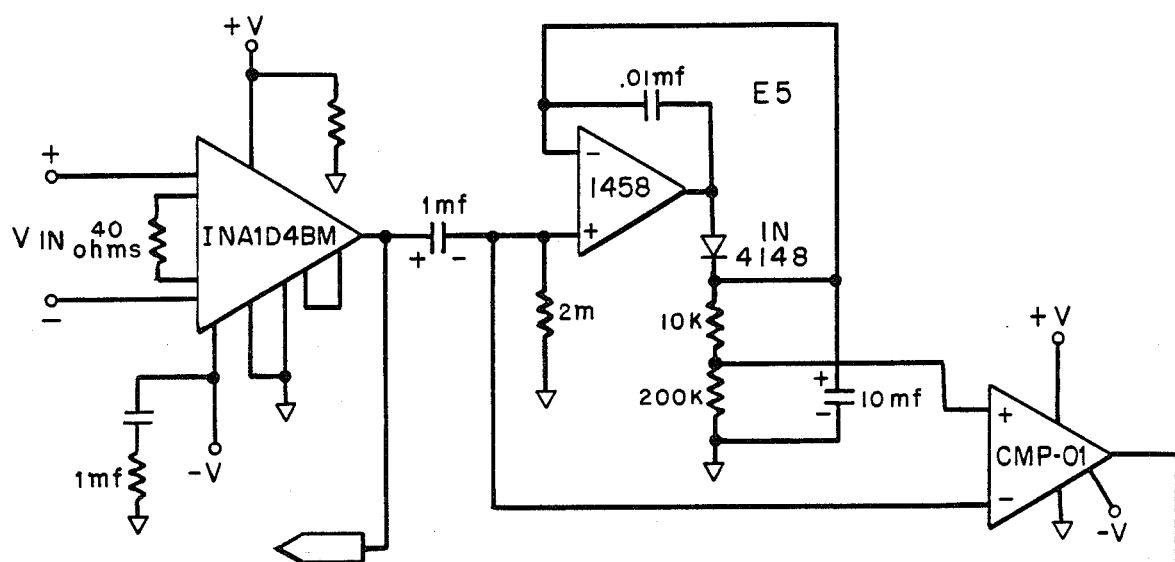
Figure 20:
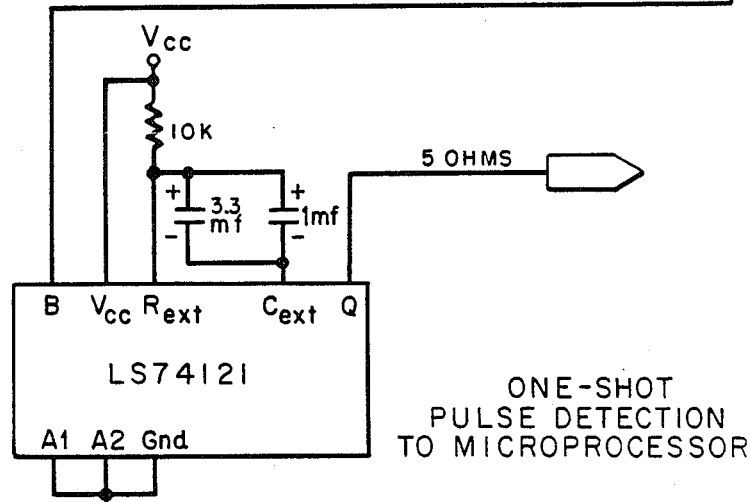
Figure 20:
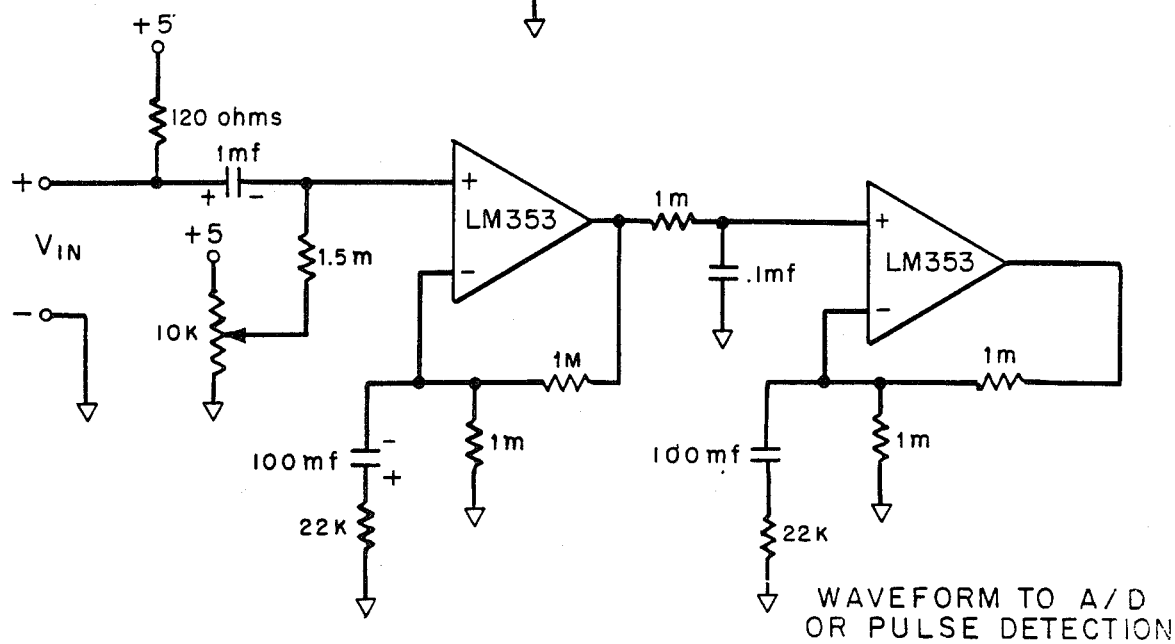

Those skilled in the art will recognize that a wide variety of conventional components can be used for each of the devices 12–42 described above, and the details of construction of these devices form no part of the present invention. Suitable ECG sensors, oximetric finger probes, impedance sensors, respiration strain gauges, blood pressure cuffs, and pressure sensors are all well known to those skilled in the art. Furthermore, a wide variety of pulse detectors can be used to perform the functions described above. Simply by way of example, the electronic circuit shown in FIG. 19 can be used for the pulse detector 26; the electronic circuit shown in FIG. 18 can be used for the pulse detector 28, and can be modified by tuning resistor values for the pulse detectors 32 and 42; the circuit shown in FIG. 17 can be used to implement the impedance sensor 20; and the circuit shown in FIG. 20 can be used to implement the respiration strain gauges 22. The circuits of FIGS. 17–20 have been provided merely by way of illustration, and they are in no way intended to limit the scope of this invention. It is anticipated that many applications of the inventions described herein will utilize circuitry which differs significantly from that of FIGS. 17–20.

The microcomputer 12 is programmed to process the input signals described above to generate reliable measures of heart rate, respiration rate, blood pressure, and blood pressure waveform. The following detailed discussion will take up these four aspects of the monitor 10 in sequence.

HEART RATE MONITORING

Figure 2:
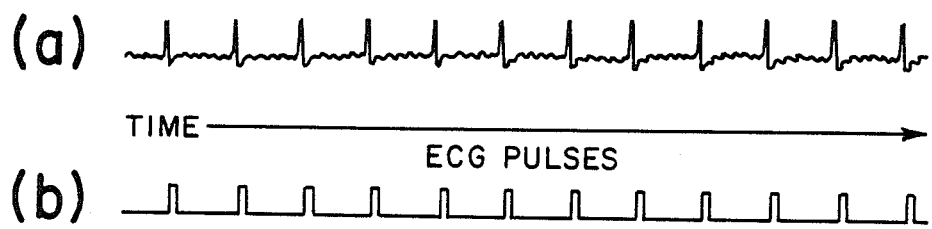
FIGS. 2a, 2b; 3a, 3b; 4a, 4b; 5a, 5b; 6a, 6b; and 7a, 7b, are signal waveforms related to the heart rate monitoring system of the monitor of FIG. 1.
Figure 3:
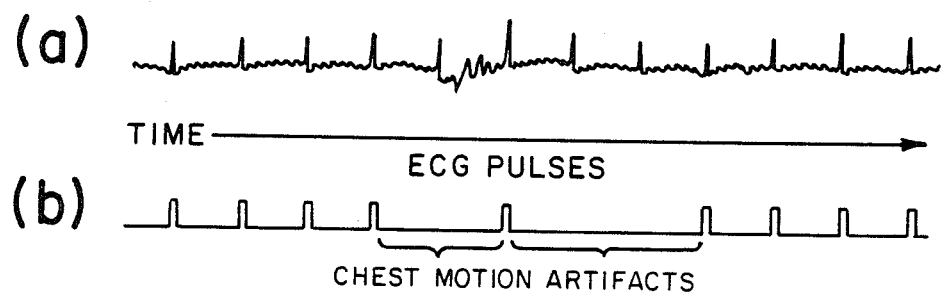
Figure 4:
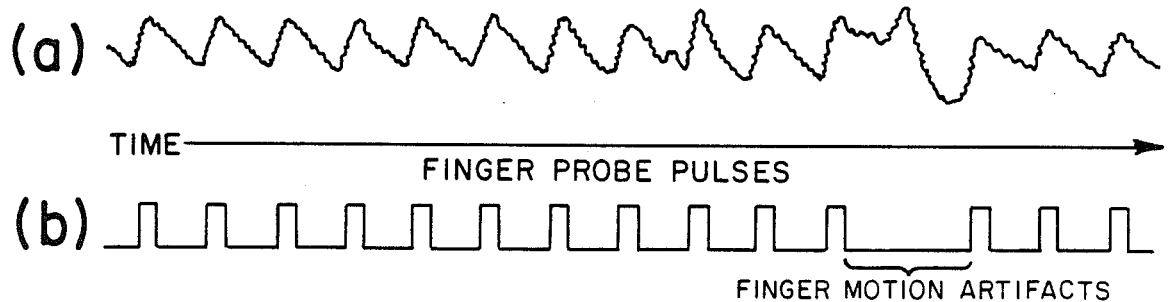
Figure 5:
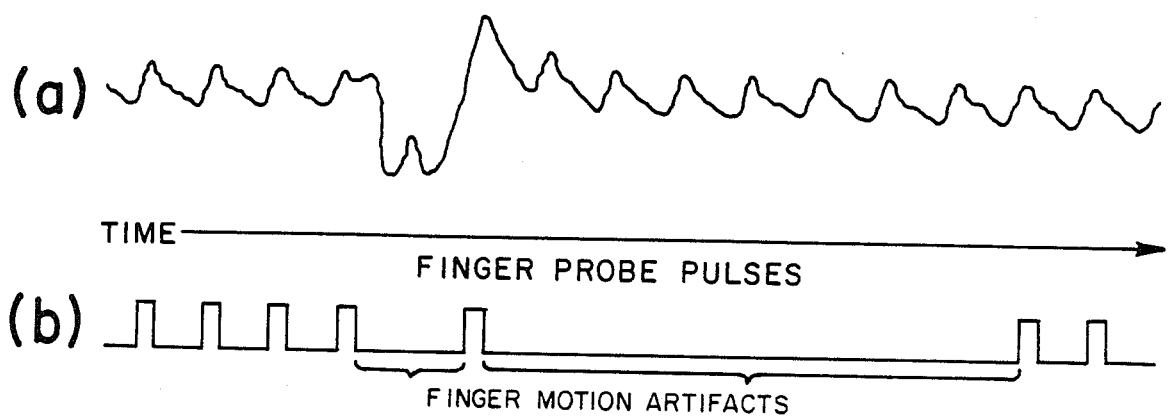
Figure 6:
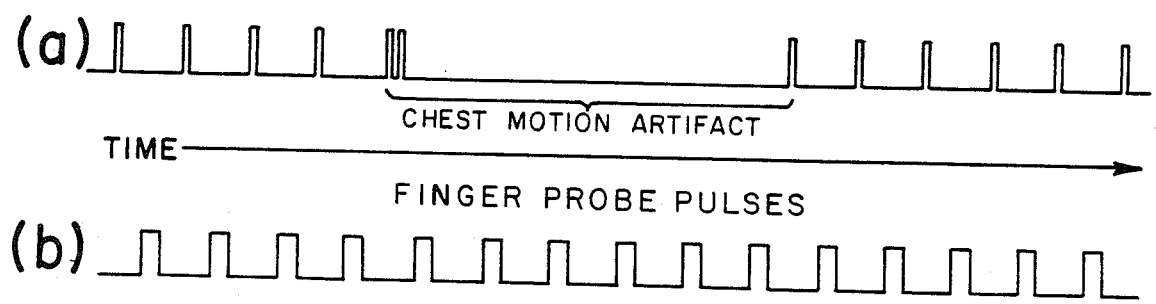
Figure 7:
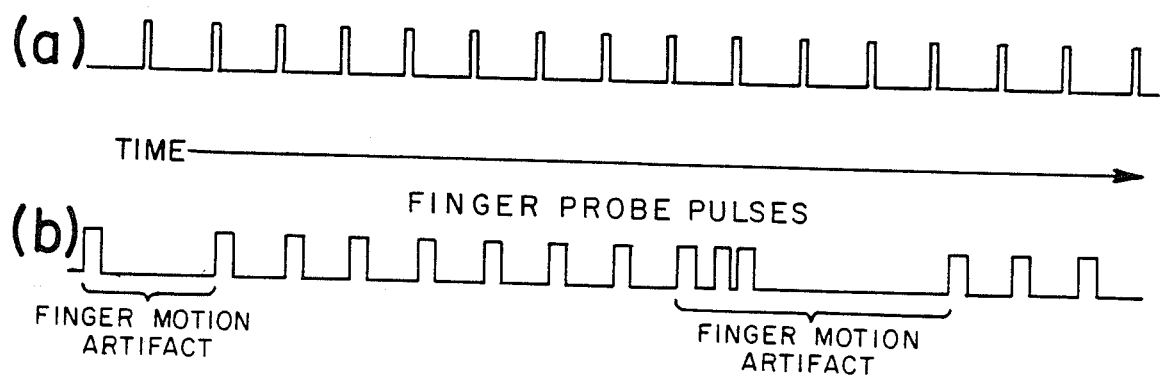

FIGS. 2a–7b provide pairs of signal waveforms that will be used to explain the principle of operation used in heart rate monitoring. Within each pair of waveforms the time base is identical; thus, FIGS. 2a and 2b represent the same time interval, and vertically aligned portions of the two waveforms correspond to the same instant in time. The signals labeled "ECG Waveform" were taken from conductor 44 of FIG. 1 and the signals labeled "ECG Pulses" were taken from conductor 46. Similarly, the signals labeled, "Finger Probe Waveform" were taken from conductor 48 and the signals labeled "Finger Probe Pulses" were taken from conductor 50.

FIGS. 2a and 2b show a typical ECG waveform and the ECG pulses derived therefrom. In the absence of artifacts such as those associated with chest motion, the ECG pulses are regular and periodic. However, as shown in FIGS. 3a and 3b, the ECG waveform can be distored by chest motion. Such distortions can cause the pulse detector 26 to fail to detect pulses in the ECG waveform associated with cardiac pulses of the subject. In the waveform of FIG. 3b, two chest motion artifacts are noted.

FIGS. 4a and 5a show the waveform generated by the oximetric finger probe 18. This waveform is normally regular and periodic, but finger motion can distort the waveform. FIGS. 4b and 5b show pulse trains generated by the pulse detector 28. These pulse trains can be interrupted by finger motion, and Figures 4b and 5b have been marked to show such finger motion artifacts.

FIGS. 6a, 6b and 7a, 7b show the ECG pulses and the finger probe pulses for two time intervals. In the time interval of FIGS. 6a and 6b the finger probe pulses are regular and periodic throughout the time interval, while the ECG pulses are interrupted by a chest motion artifact. Conversely, during the time interval shown in FIGS. 7a and 7b, the ECG pulses are regular and periodic while the finger probe pulses are interrupted by finger motion artifacts. These waveforms show that the accuracy of the information in either the ECG channel or the finger probe channel may be compromised, by chest motion and coughing on the one hand and by finger motion on the other hand. However, in many cases the pulse information derived from the oximetric finger probe at the fingertip is not disturbed at the same time as is the pulse information derived from the ECG sensor.

According to this invention the microprocessor monitors the pulse trains generated by both of the pulse detectors 26 and 28 and selects the pulse train with the more accurate information as the better indicator of heart rate. The general approach is to chose the channel having the signal with the more regularly repeating pulse intervals. In this way, the information provided by two separate sensors in interrelated and combined to provide an improved heart rate measurement.

Figure 8A:
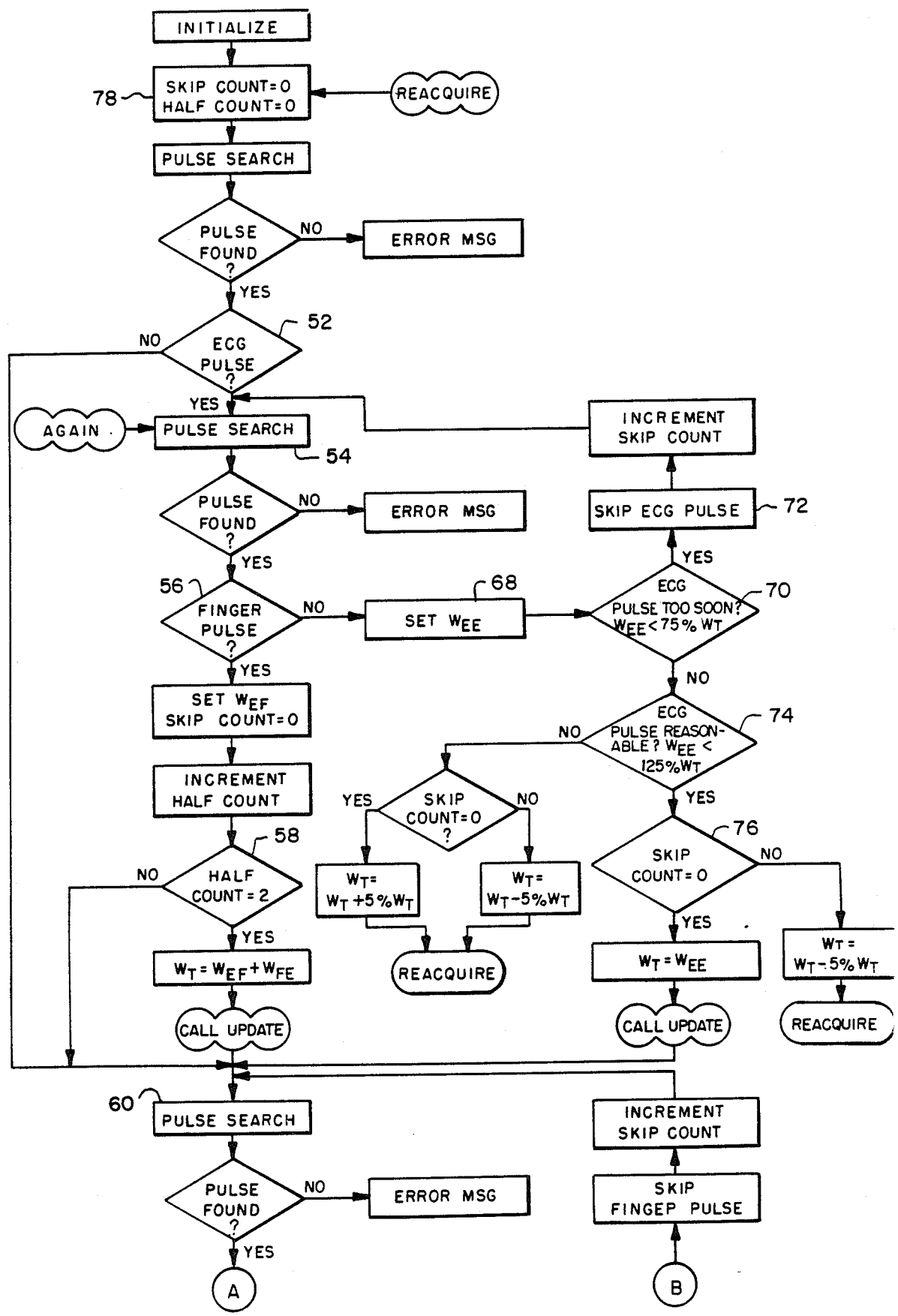
FIGS. 8a-8c are flow charts of a first version of the heart rate monitoring system of the monitor of FIG. 1.
Figure 8B:
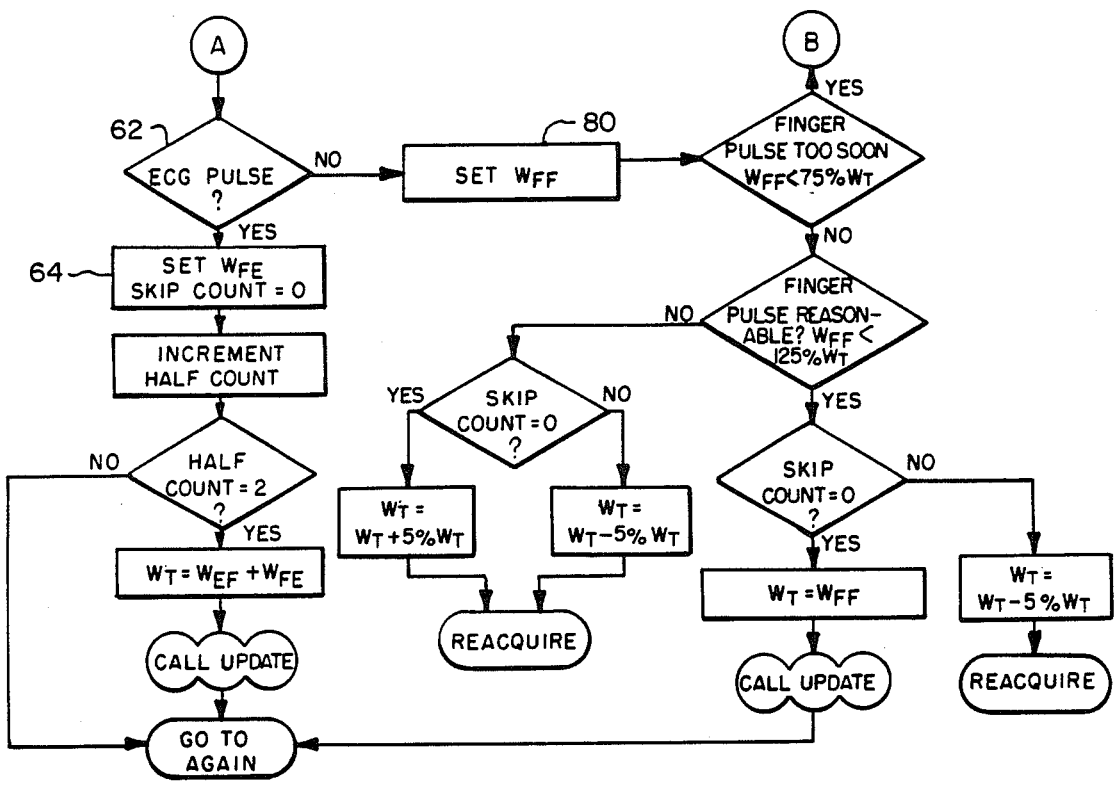
Figure 8C:
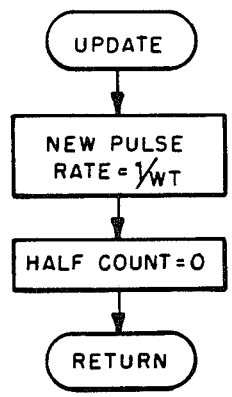

FIGS. 8a-8c provide a flow chart of a first preferred embodiment of a program for interrelating the ECG and finger probe pulses.

The program of FIGS. 8a, 8b begins by initializing internal variables and setting the variables Skip Count and Half Count to zero. A pulse search routine is then executed which searches for pulses generated by either of the pulse detectors 26, 28. Once a pulse is found, the program branches at decision diamond 52, depending upon whether the pulse found is an ECG pulse or a finger pulse.

Assuming the pulse is an ECG pulse, the program then searches in block 54 for a next pulse. Once the next pulse is found the program branches at decision diamond 56, depending upon whether this next pulse is a finger pulse or an ECG pulse.

During normal operation, ECG pulses will alternate with finger pulses. Assuming this to be the case the variable $W_{EF}$ (equal to the time window from an ECG pulse to a next adjacent finger pulse) is set equal to the measured interval and Skip Count is set equal to zero. Then the variable Half Count is incremented and checked at decision diamond 58. In the first pass through the program Half Count would be equal to 1 and control would then branch to a next pulse search as indicated at block 60. Once a pulse is found in block 60, control branches at decision diamond 62, depending upon whether this pulse is an ECG pulse or a finger pulse.

If both the ECG channel and the finger probe channel are functioning properly, and if the previous pulse was a finger pulse, this pulse should be an ECG pulse. If so, the variable $W_{FE}$ (equal to the time window from a finger pulse to the next adjacent ECG pulse) is set in block 64 and the variable Skip Count is set to zero. Then the variable Half Count is incremented and is compared with the constant 2. If Half Count equals 2, indicating that both $W_{EF}$ and $W_{FE}$ have been set, then the variable $W_T$ is set equal to $W_{EF}$ plus $W_{FE}$ in block 66. $W_T$ is indicative of the total time interval for a heartbeat, and in this branch of the program is equal to the sum of the time from an ECG pulse to the next adjacent finger pulse, and from that finger pulse to the next adjacent ECG pulse.

Once $W_T$ has been set in block 66 the subroutine Update is called. As shown in FIG. 8c, this subroutine sets a new pulse rate equal to the inverse of $W_T$, resets Half Count to zero, and then returns. Control is then returned to block 54.

In the event that no finger pulse is detected between two adjacent ECG pulses, then the program branches at decision diamond 56 to block 68, at which the variable $W_{EE}$ is set equal to the time window or interval between two adjacent ECG pulses. The variable $W_{EE}$ is then compared in decision diamond 70 with a value equal to 75% of the most recent value of $W_T$. If $W_{EE}$ is less than this value, indicating that the current ECG pulse has occurred too soon and is therefore probably an artifact, control branches at decision diamond 70 to block 72, which skips the current ECG pulse and increments Skip Count. Control is then returned to block 54.

In the event that the comparison in the decision diamond 70 indicates that the most recent ECG pulse has not occurred earlier than the allowed window, then $W_{EE}$ is then compared for reasonableness in decision diamond 74. If $W_{EE}$ is less than 125% of the most recent value of $W_T$, then Skip Count is checked in decision diamond 76. If Skip Count is equal to zero then $W_T$ is set equal to $W_{EE}$ and the subroutine Update is called. On the other hand, if Skip Count is not equal to zero (indicating one or more skipped pulses), then $W_T$ is reduced by 5% and control is returned to block 78. If $W_{EE}$ is greater than 125% of $W_T$ (and therefore outside of the expected range), then $W_T$ is either incremented or decremented by 5%, depending upon the state of the variable Skip Count, and control is returned to block 78.

In general terms, the portion of the program associated with blocks 68 through 76 is only executed when two adjacent pulses are ECG pulses. In this case $W_{EE}$ is set, compared with upper and lower values, and then used to update $W_T$ if Skip Count is zero. If $W_{EE}$ is either too small or too large, $W_T$ is modified without calling the routine Update in order to bring $W_T$ more nearly equal to $W_{EE}$.

Similarly, if two adjacent pulses are finger pulses, then control branches at decision diamond 62 to block 80, which sets the variable $W_{FF}$ (the time window or interval between two adjacent finger pulses), compares $W_{FF}$ with upper and lower limits as described above, checks the variable Skip Count, and then sets $W_T$ equal to $W_{FF}$ in the event $W_{FF}$ is reasonable and Skip Count is zero. The portion of the program associated with block 80 operates identically to that associated with block 68, except that block 80 relates to the use of two adjacent finger pulses to set the variable $W_{FF}$.

From the foregoing description it should be apparent that the program of FIGS. 8a, 8b automatically selects the pulse train with the more regular waveform for use in updating the variable $W_T$ and therefore the measured pulse rate. In the event both the ECG channel and the finger probe channel are functioning properly, the ECG and finger pulses alternate in time and the variables $W_{EF}$ and $W_{FE}$ are summed to obtain $W_T$, the total time between pulses and the reciprocal of the new pulse rate. On the other hand, if either the ECG pulses or the finger pulses drop out (due to a motion artifact, for example), the program of FIGS. 8a, 8b selects the remaining pulse train and then measures the interval between adjacent pulses in the remaining pulse train to set to set $W_T$ and therefore the new pulse rate.

The program of FIGS. 8a, 8b operates on a pulse by pulse basis to determine the more regular pulse train. This is not a requirement for all embodiments of this invention, and FIG. 9 shows an alternative program which operates with groups of pulses.

Figure 9:
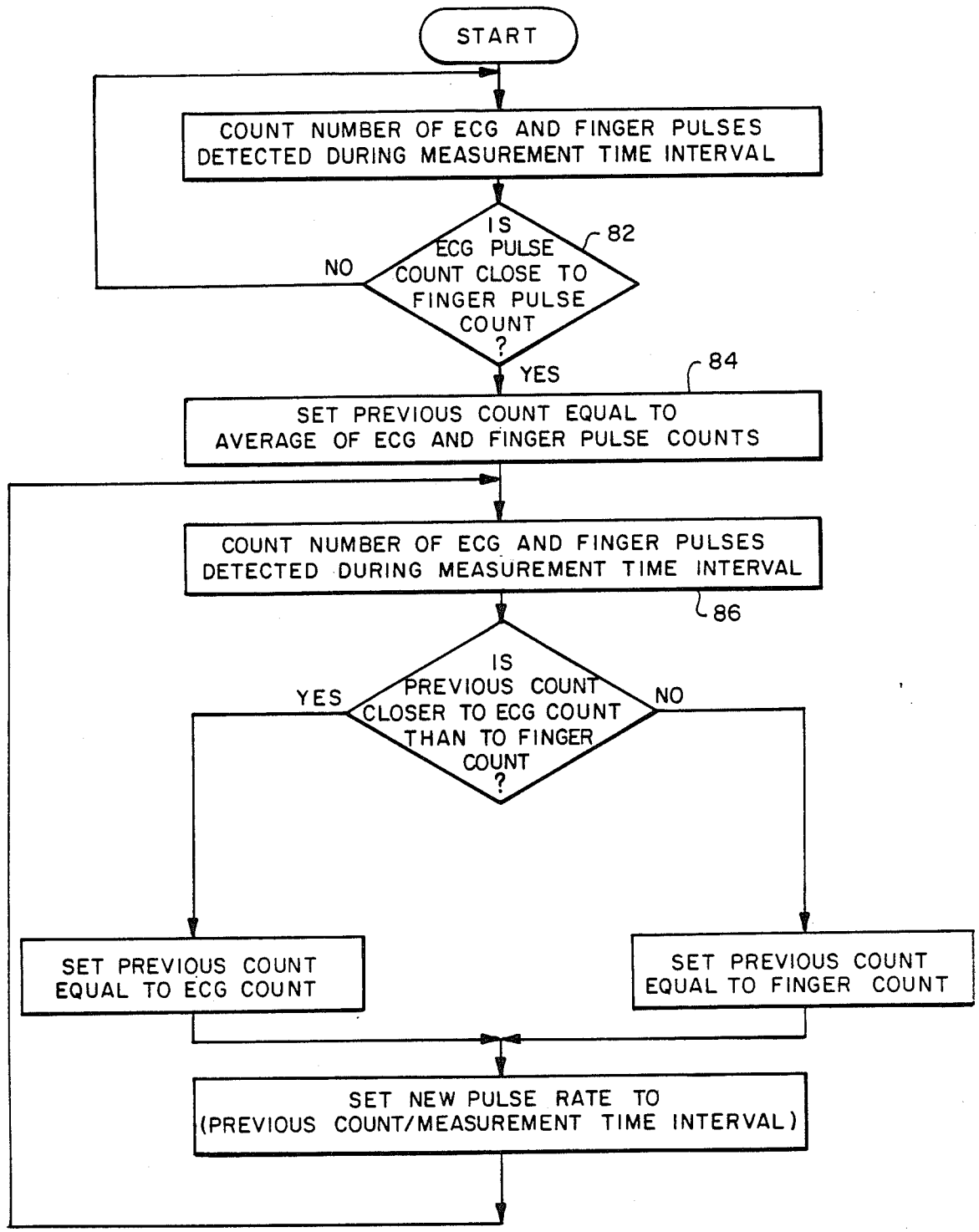
FIG. 9 is a flow chart of a second version of a heart rate monitoring system suitable for use in the monitor of FIG. 1.

The program of FIG. 9 first counts the number of ECG pulses and the number of finger pulses detected during a preset measurement time interval. The measured ECG pulse count is then checked to determine whether it is close to the measured finger pulse count in decision diamond 82. If not, the count is repeated until the ECG pulse count is within the desired tolerance of the finger pulse count. Once this is the case, the variable Previous Count is set equal to the average of the ECG and finger pulse counts in block 84. The program then counts in block 86 the number of ECG and finger pulses detected during a next measurement time interval, which is equal in duration to the previous measurement time interval. Control then branches depending upon whether the variable Previous Count is closer to the ECG count or to the finger count of block 86. If Previous Count is closer to the ECG count then Previous Count is set equal to the ECG count. Conversely, if Previous Count is closer to the finger count, then Previous Count is set equal to the finger count. In either case, the new pulse rate is set equal to the updated Previous Count divided by the measurement time interval, and control is returned to block 86.

The program of FIG. 9 monitors the ECG pulses and the finger pulses occurring during the measurement time interval and automatically chooses the pulse train having a pulse count which more nearly corresponds to the previous pulse count. In this way, the more periodic and regular pulse train is selected for use in determining the new pulse rate.

In both the programs of FIGS. 8a, 8b and the program of FIG. 9 the ECG and the finger probe pulse train are interrelated and the pulse train with the more regular pattern is selected to provide an improved, more reliable, more artifact-free measure of heart rate. Of course, this invention is not restricted to use with finger probes and ECG sensors. Rather, any two measures of pulse rate can be used, such as pulse sensors of the type which include an occluding cuff or which monitor ECG, chest impedance, or some other parameter from which pulse information may be derived. In addition the heart rate monitoring system described above can be used in monitors which do not measure respiration rate or blood pressure.

RESPIRATION MONITORING

The vital signs monitor 10 includes an impedance sensor 20 and a strain gauge 22, as described above. The outputs of these two sensors are combined to produce a particularly reliable measure of respiration rate.

Figure 10:
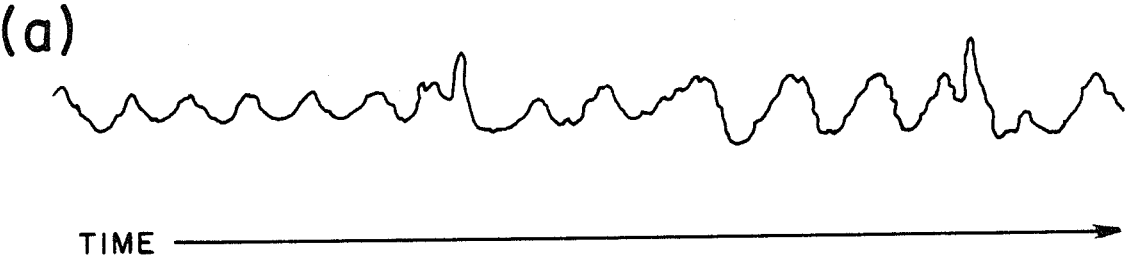
FIGS. 10a and 10b are signal waveforms related to the respiration rate monitoring system of the monitor of FIG. 1.
Figure 10:
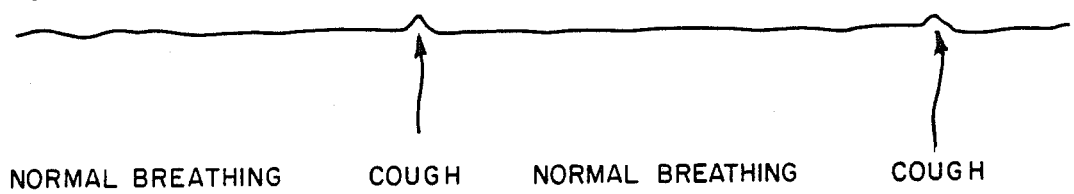

The impedance sensor 20 measures the fluctuating electrical impedance associated with the changing volume of the chest of the subject. The strain gauge 22 mechanically monitors the physical changes in chest dimension. Both of these measuring techniques are subject to artifacts associated with chest motion such as coughing. FIGS. 10a and 10b show the signal outputs of the impedance sensor 20 and the strain gauge 22, respectively, for a preset measuring interval. The impedance waveform of FIG. 10a includes regular peaks associated with respiration, as well as additional peaks associated with coughs. The peaks associated with coughs are only slightly greater in amplitude than the peaks associated with normal respiration, and it is difficult to distinguish reliably between these two types of peaks in the impedance waveform. However, as shown in FIG. 10b, the artifacts associated with chest motion stand out clearly in the strain gauge waveform. The microcomputer 12 is programmed to use the strain gauge waveform as a measure of chest motion artifacts in order to correct the breathing rate as determined by the impedance waveform.

Figure 11A:
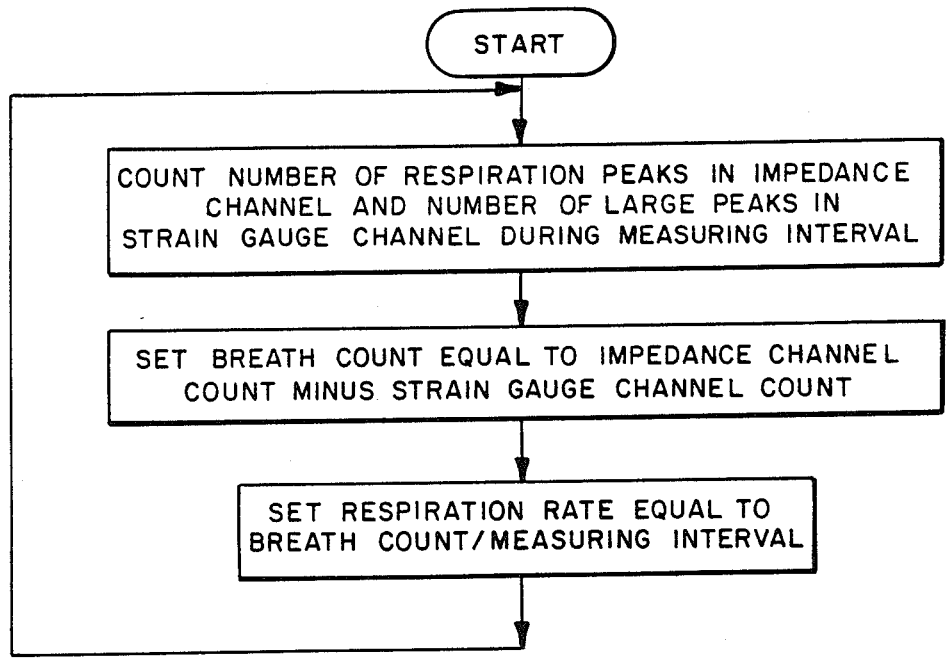
FIG. 11a is a flow chart of the respiration rate monitoring system of the monitor of FIG. 1.

This program is flowcharted in FIG. 11a. As shown in FIG. 11a the first step is to count the number of respiration peaks in the impedance channel and the number of large peaks associated with chest motion artifacts in the strain gauge channel during a preset measuring interval. Then the variable Breath Count is set equal to the impedance channel count minus the strain gauge channel count, and finally the respiration rate is set equal to the Breath Count divided by the measuring interval. By combining the impedance waveform with the strain gauge waveform as described above, a more accurate measure of respiration rate is obtained.

Figure 11B:
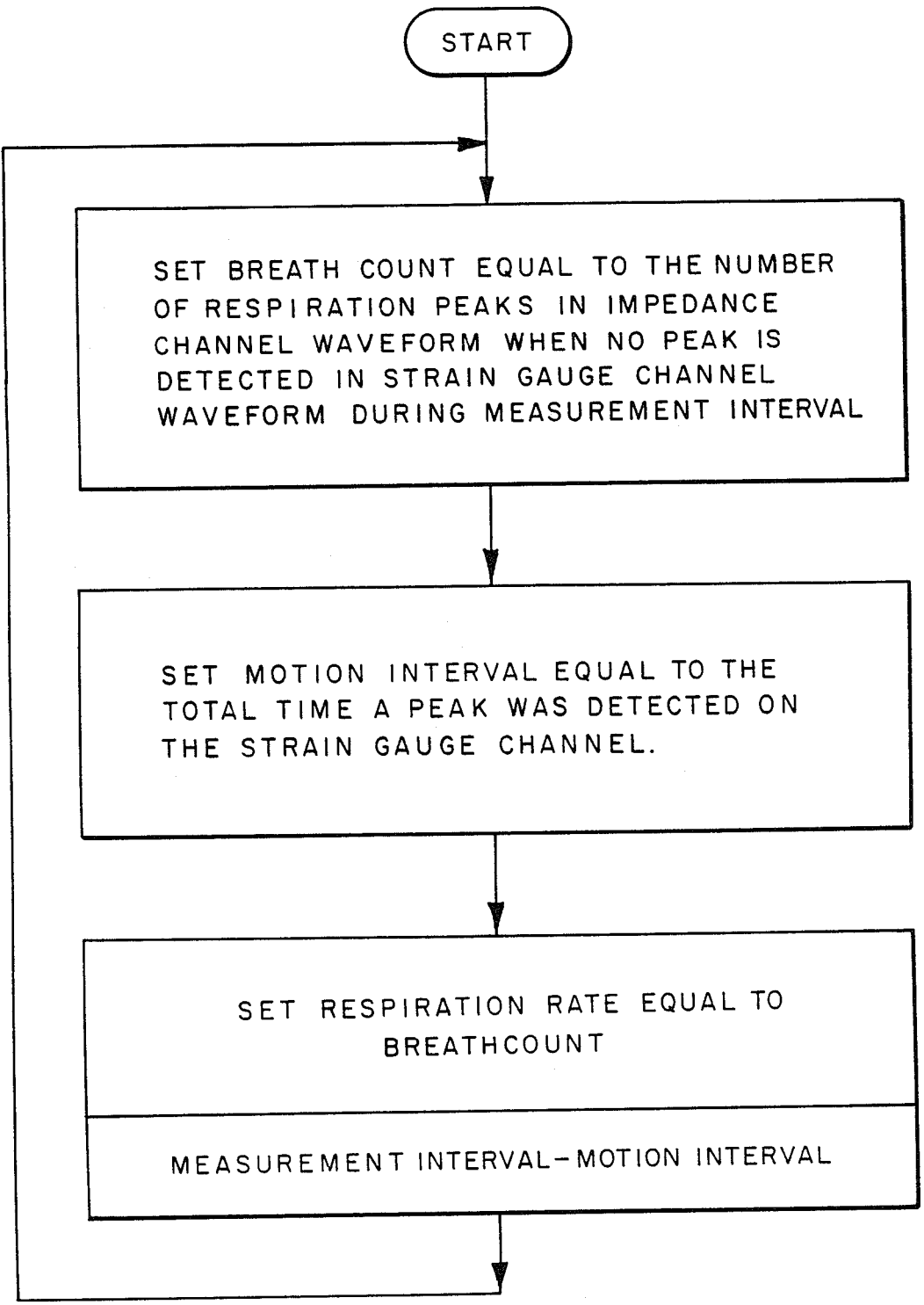
FIG. 11b is a flow chart of an alternate respiration rate monitoring system.

Another algorithm which can be used to obtain an accurate measure of respiration rate is flowcharted in FIG. 11b. With this algorithm, the variable BREATH COUNT is used to count peaks on the impedance channel waveform during a measuring period having a time duration equal to MEASUREMENT INTERVAL. In order to suppress artifacts associated with chest motion, BREATH COUNT is not incremented during periods of unusual chest motion, as indicated by the presence of a large peak on the strain gauge channel. Furthermore, the total duration of the periods of unusual chest motion is measured and stored in the variable MOTION INTERVAL. The respiration rate is then set equal to BREATH COUNT divided by the actual time period of measurement (MEASUREMENT INTERVAL—MOTION INTERVAL).

As before, this invention is not restricted to use with the particular sensors described above. For example, piezoelectric films can be used to measure changes in chest dimension and electromyograms can be used to measure muscle potentials of the lower chest in place of the strain gauges described above. In addition, air flow sensors such as microphones on the trachea, flow meters on an airway, and thermistors; $CO_2$ sensors in expired air; and other types of sensors can be substituted for the impedance channel described above. Furthermore, the respiration rate monitoring system described above can be used in monitors which do not measure heart rate or blood pressure.

BLOOD PRESSURE MONITORING

The vital signs monitor 10 also determines blood pressure of the subject, this time by combining pressure information from the blood pressure cuff 34 with pulse information from the oximetric finger probe 18.

In general terms, the blood pressure cuff 34 is inflated to a level higher than the systolic blood pressure, until arterial pulsations in the fingertip (as measured by the oximetric finger probe 18) cease. The occluding cuff 34 on the arm is then gradually deflated. Once the cuff pressure drops below the systolic blood pressure, blood flow resumes beneath the cuff. This immediately causes a pulsation detected by the oximetric finger probe 18 at the fingertip, and it is the appearance of this first pulsation that signals that the cuff has dropped to systolic pressure. The microcomputer 12 reads the systolic pressure from the pressure sensor 24. As the pressure in the cuff 34 continues to decrease below the systolic pressure, pulsations are received by the microcomputer 12 from both the pressure sensor 24 associated with the cuff 34 and from the oximetric finger probe 18. The pulses arriving at the fingertip occur shortly after the pulses appearing at the cuff. There are two factors which contribute to this delay. First, it takes a period of time for the pulse to propagate from the upper arm to the fingertip. Second, the partial occlusion of the artery, due to the pressure in the cuff 34 having a value below systolic and above diastolic, causes a delay in the pulse below the cuff. The second factor is dependent upon the difference between cuff pressure and diastolic pressure. As the cuff pressure drops closer to the diastolic pressure, the second type of delay decreases, and when the cuff pressure falls below diastolic pressure, the second type of delay is no longer a factor. Therefore, once the cuff pressure falls below the diastolic blood pressure, the delay between the cuff pulse and the finger probe pulse becomes substantially constant.

Figure 13:
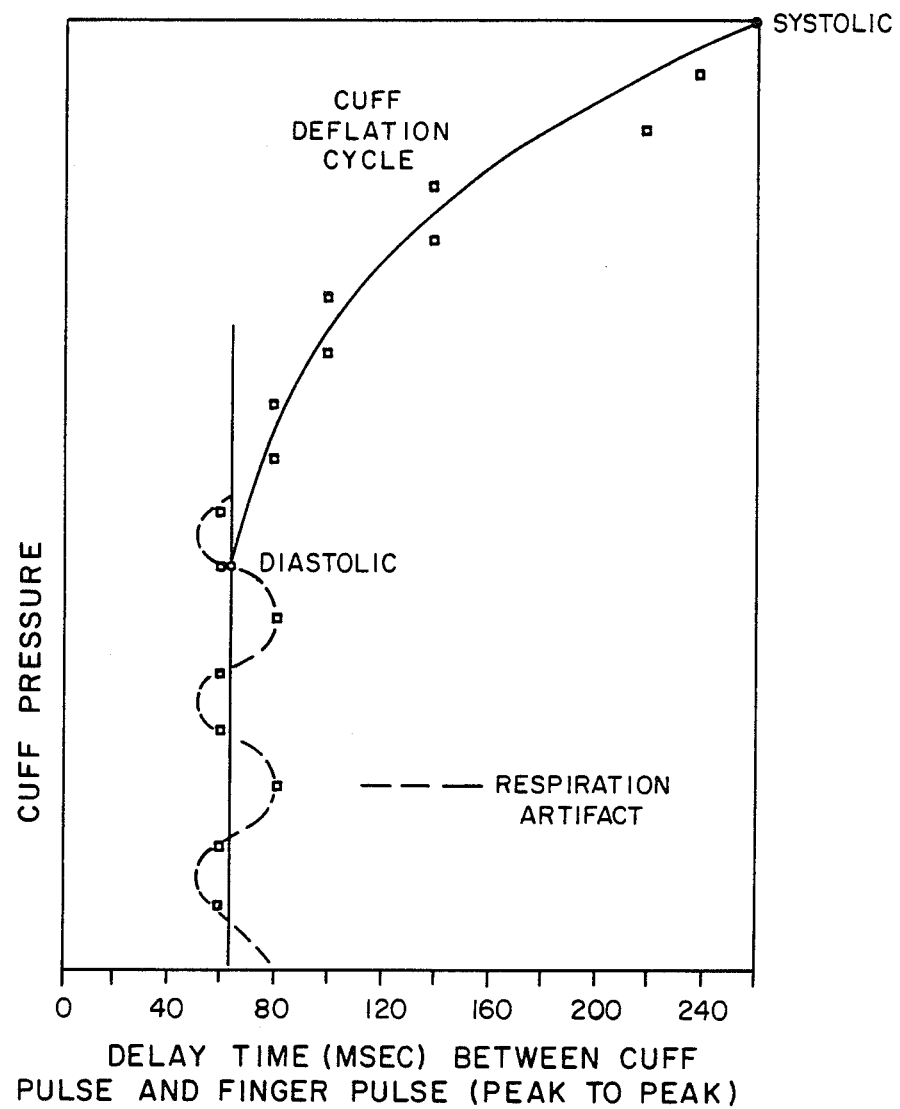
FIG. 13 is a graph of the time delay between the blood pressure cuff pulse and the finger probe pulse as a function of the pressure of the blood pressure cuff.

FIG. 13 is a graph showing the time delay between (1) the arm pulse as detected by the pressure sensor 24 and the pulse detector 42 and (2) the finger pulse as detected by the oximetric finger probe 18 and the pulse detector 28, as a function of the pressure of the blood pressure cuff 34. As shown in FIG. 13, when the cuff pressure is just below systolic pressure there is a delay of about 260 milliseconds between the cuff pulse and the finger pulse. As the cuff pressure decreases to the diastolic value, the delay decreases to a value of about 65 milliseconds. As the cuff pressure further decreases below diastolic, the delay is not decreased, but simply oscillates around the 65 millisecond value. As the cuff deflates, the transition from a decreasing delay to a fixed delay indicates the diastolic pressure value.

The oscillations in the delay value (which are most easily seen when the cuff pressure is below diastolic) are synchronous with the subject's respiratory cycle. Previous work has shown that these oscillations are due to variations in cardiac stroke volume which occur as a result of fluctuations in intrathoracic pressure during the respiratory cycle.

Figure 12:
FIGS. 12a and 12b are signal waveforms related to the blood pressure monitoring system of the monitor of FIG. 1.
Figure 12:
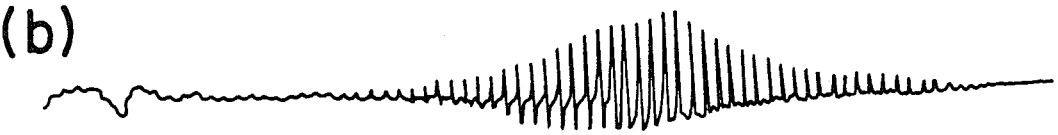
Figure 14:
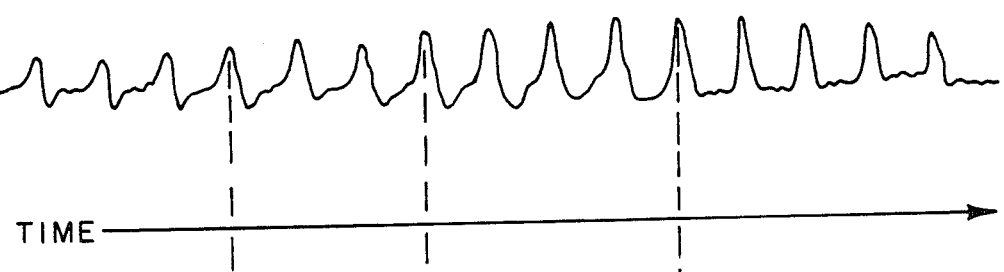
FIG. 14a and 14b are signal waveforms related to the blood pressure monitoring system of the monitor of FIG. 1.
Figure 14:
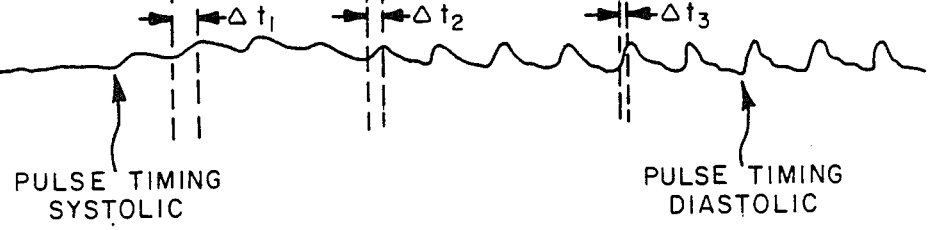

FIGS. 14a and 14b show waveforms associated with oscillations in pressure of the cuff 34 and oscillations in the signals generated by the finger probe 18, respectively. The waveform of FIG. 14a is similar to that of FIG. 12b, except that the time scale of FIG. 14a has been expanded to enable more careful analysis of pulse timing. The left hand portions of the waveforms of FIGS. 14a and 14b illustrate the suppression of pulses at the fingertip when the cuff pressure is higher than the systolic pressure. As the pressure drops to the systolic level, the trace of FIG. 14b begins to indicate arterial pulsations at the fingertip. The arrival of this first pulse is an indication that the instantaneous pressure indicated by the pressure sensor 24 corresponds to systolic blood pressure of the subject. In the center portion of FIGS. 14a and 14b both waveforms indicate the presence of pulsations as the cuff pressure drops from the systolic to the diastolic. Careful examination of the timing differences between pulses in FIGS. 14a and 14b show the progressive decrease in the delay time as described above in conjunction with FIG. 13. After the cuff pressure reaches diastolic, the right hand portion of the waveforms of FIGS. 14a and 14b illustrate the substantially constant delay between the respective pulses. Thus, the data shown in FIGS. 14a and 14b provide the necessary information for determining both the systolic and the diastolic blood pressure through the use of interrelationships between cuff pulsations detected by the pressure sensor 24 and fingertip pulsations as detected by the oximetric finger probe 18.

Figure 15:
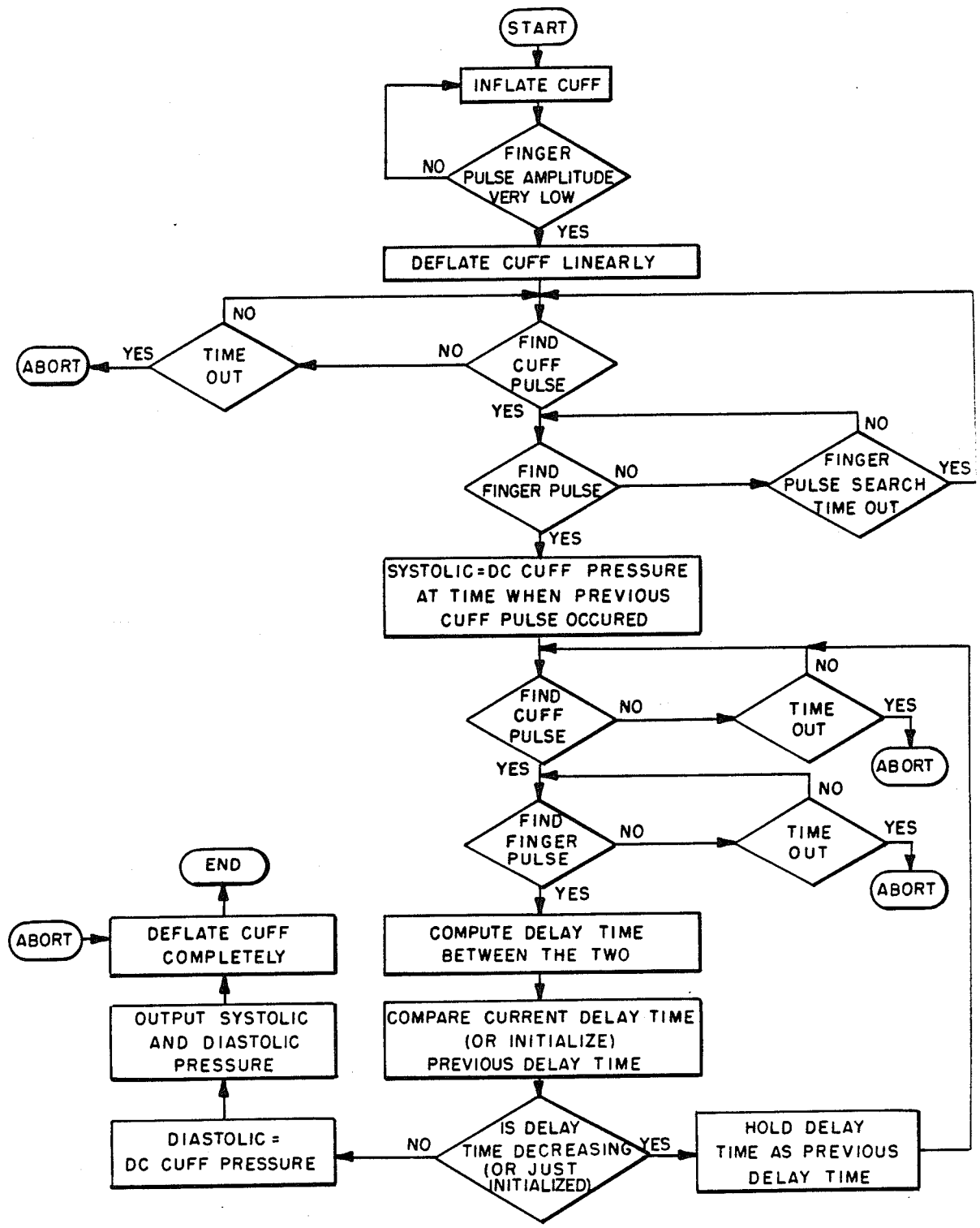
FIG. 15 is a flow chart of the blood pressure monitoring system of the monitor of FIG. 1.

FIG. 15 shows a flowchart of a suitable program for implementing the blood pressure monitoring technique described above. As shown in FIG. 15 the first step is to inflate the blood pressure cuff 34 until the amplitude of the pulses detected by the oximetric finger probe 18 is at very low level. This is used to determine that the pressure of the cuff 34 is above systolic. Then the cuff 34 is deflated at a rate such as 3 millimeters of mercury per second.

The microcomputer 12 then monitors the pulse detector 42 for cuff pulses. If no cuff pulses are found within an allowed time, the routine aborts. Otherwise, the routine then monitors the pulse detector 28 for finger probe pulses. Once a finger probe pulse is found, the microcomputer sets the systolic pressure equal to the DC cuff pressure at the time when the previous cuff pulse occurred. The routine then monitors the pulse detector 42 for additional cuff pulses and the pulse detector 28 for additional finger pulses. The delay time between each cuff pulse and the subsequent finger pulse is then calculated and compared with the previous delay time. As long as the newly calculated delay time is less than the previous delay time, the routine sets the previous delay time to the newly calculated delay time and returns to search for more cuff and finger pulses. However, in the event the newly calculated delay time is equal to or greater than the previous delay time, then the diastolic pressure is set equal to the currently prevailing DC value of the cuff pressure as measured by the pressure sensor 24 and the A/D converter 40.

Once systolic and diastolic pressures have both been measured, the cuff is deflated completely and the routine terminates.

It is important to note that the foregoing technique for blood pressure measurement does not increase the hardware complexity of the vital signs monitor 10 in any way. The oximetric finger probe 18 and the pulse detector 28 are present in the vital signs monitor 10 for other purposes, and therefore the present invention provides important improvements in accuracy over the prior art oscillometric technique without increasing the cost or hardware complexity of the vital signs monitor 10.

Once again, this system is not restricted to use with the particular sensors described above. Other pulse detectors can be substituted for the oximetric finger probe to detect pulses distal to the cuff, and other pulse detectors can be used to detect pulses at or near the cuff. In addition, the blood pressure monitoring system described above can be used in monitors which do not measure heart rate or respiration rate.

BLOOD PRESSURE WAVEFORM MONITOR AND VASOMOTOR ACTIVITY DETECTOR

It is well known that oximetric sensors such as the oximetric finger probe 18 provide excellent relative measures of the blood pressure waveform. However, standard oximetric waveforms are not calibrated as to core blood pressure, and this lack of calibration is a significant limitation in many settings. The monitor 10 overcomes this problem by automatically combining core blood pressure information derived from an indirect blood pressure measuring system such as that described in the preceding section with waveform information derived from a waveform detector such as the oximetric finger probe 18. By providing an electronic system such as the microcomputer 12 with signals from both sources, it is possible to generate a continuous waveform which is calibrated as to core blood pressure and which therefore is similar in many respects to the pressure signal generated by an invasive catheter blood pressure monitoring system. Pressure accuracy is ensured by updating the calibration of the waveform periodically. The period between updates is typically in the range of 15 seconds to several minutes, but it is conceivable that both longer and shorter periods may be selected. During the period between recalibrations the waveform is continuously displayed using the calibrations obtained from the most recent blood pressure measurement. As described in greater detail below, the method of this invention can detect clinical conditions in which the waveform generated by the oximetric finger probe 18 decreases in amplitude without a corresponding change in core blood pressure. This condition can provide an early warning of circulatory failure.

Turning now to FIGS. 16a-16e, the monitor 10 is programmed to implement the waveform display and vasomotor monitoring techniques described above. As described above, the monitor 10 includes an oximetric finger probe 18 which produces on line 48 a waveform which is uncalibrated as to blood pressure but which has a shape that closely tracks the blood pressure waveform of the subject. The signal output of the oximetric finger probe 18 is digitized by the A/D converter 30 and then applied as a digital input to the microcomputer 12. Similarly, the monitor 10 includes a blood pressure cuff 34, a pressure sensor 24, and related components which allow the microcomputer 12 to measure the systolic and diastolic core blood pressure of the subject as described in the preceding section. These components are used in conjunction with the program flow charted in FIGS. 16a-16e to generate a calibrated waveform indicative of core blood pressure of the subject and to monitor vasomotor activity of the subject.

Turning now to FIG. 16a, the main routine initializes, measures the core blood pressure of the subject and then sets the variables SYSTOLIC and DIASTOLIC to the measured systolic and diastolic pressures. In this embodiment systolic and diastolic pressures are measured as described in the preceding section. The routine PUlseamp (FIG. 16b) is called to measure the average peak to peak amplitude of the finger probe waveform over a 20 pulse period. Then the routine Rescale (FIG. 16c) is called in order to determine the calibration factors M and B which will be used to calibrate the displayed waveform. In general terms, the routine Rescale sets the calibration factor M equal to the ratio between (1) the difference between SYSTOLIC and DIASTOLIC and (2) the average amplitude of the finger probe waveform. The calibration factor B is set equal to the vertical offset required to place the calibrated waveform as desired on the display 14.

Figure 16C:
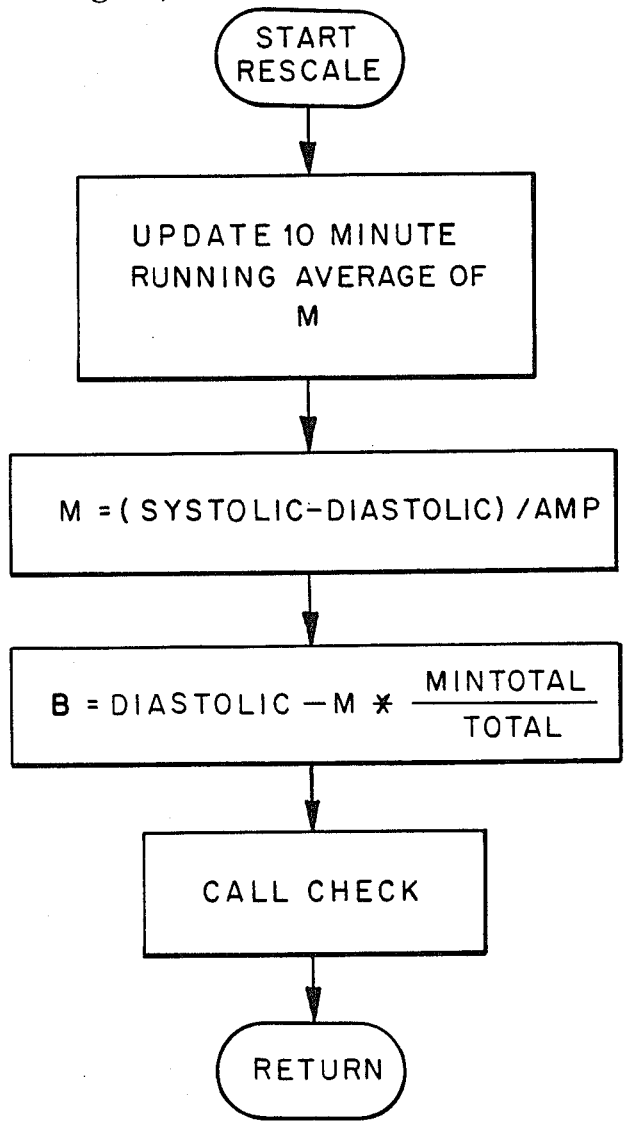
Figure 16D:
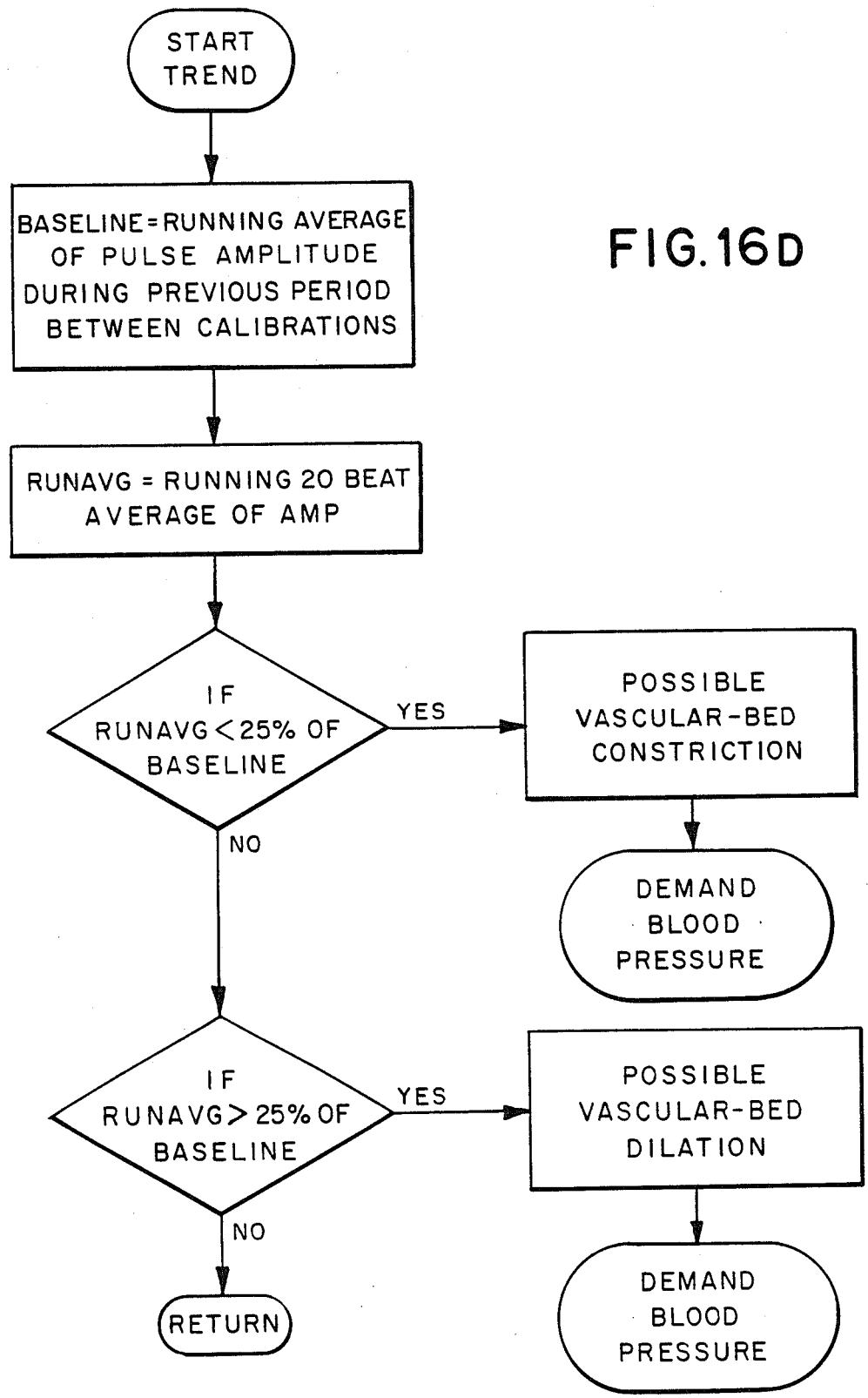
Figure 16E:
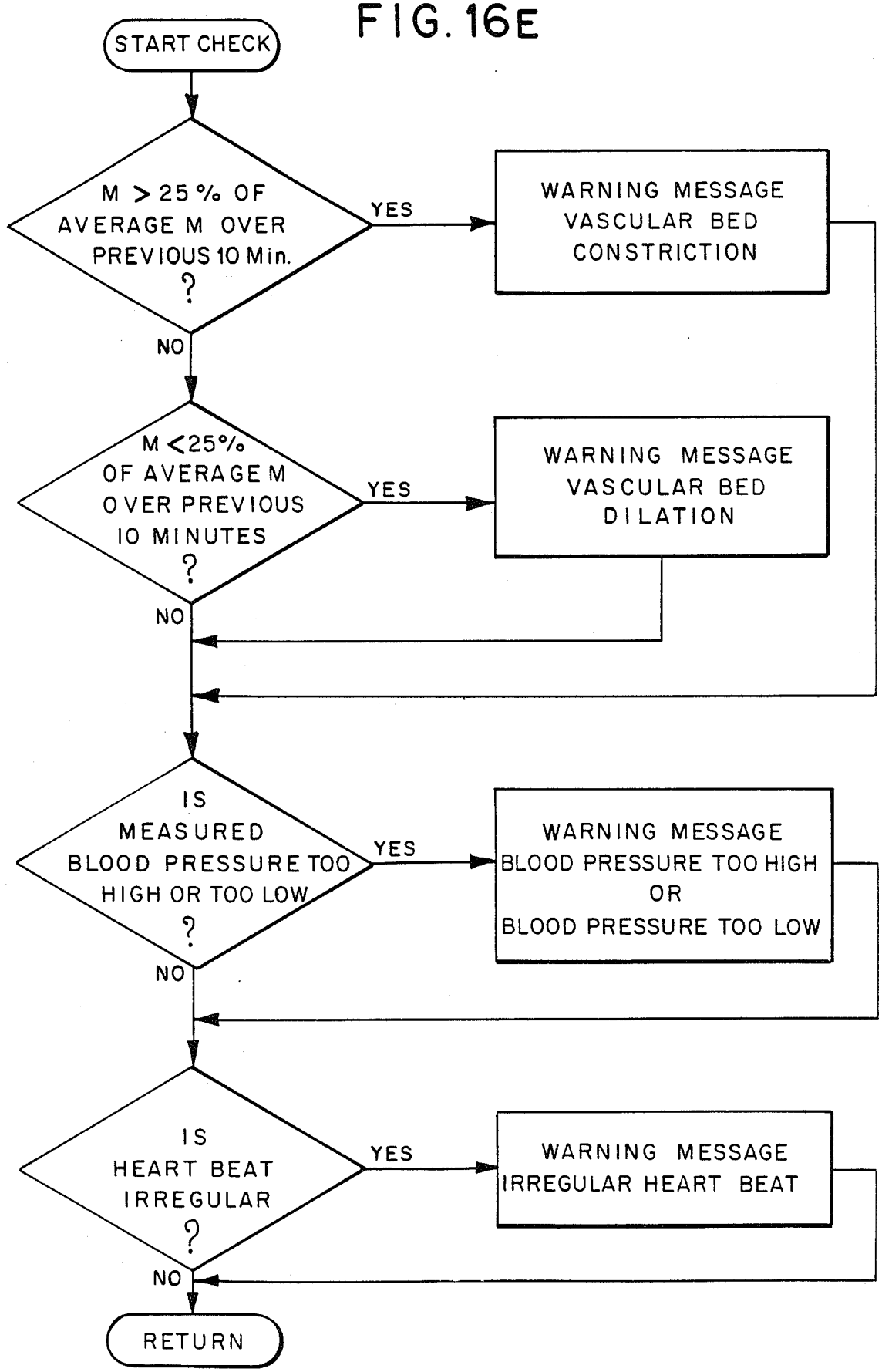

Once the calibration factors M and B have been determined in the routine Rescale, the program of 16c then calls the routine Check (FIG. 16e). The routine Check monitors for various warning conditions, and displays appropriate warning messages if appropriate. In particular, Check checks for fluctuations in M, and classifies an increase or a decrease in M of 25% or more (as compared with the average value of M over the previous ten minute period) as indicative of excessive vascular bed constriction or dilation.

At this point a timer is reset and the routine of FIG. 16a takes a reading $V_{IN}$ of the pulse waveform via the A/D converter 30. Then the value $V_{IN}$ is scaled with the calibration factors M and B according to the formula $$V_{OUT}=M(V_{IN})+B.$$

The scaled value $V_{OUT}$ is then output for display on the display 14.

The Pulseamp routine is called to measure the amplitude of the finger probe waveform for a single pulse cycle and the routine Trend (FIG. 16d) is executed. Trend maintains the variable BASELINE equal to the running average of pulse amplitude AMP during the period since the last measurement of SYSTOLIC and DIASTOLIC, and the variable RUNAVG equal to the average of AMP of the last 20 pulse cycles. In the event RUNAVG deviates from BASELINE by more than ±25%, this is taken as an indication of possible vascular bed constriction or dilation and control is returned to the block in FIG. 16a that measures SYSTOLIC and DIASTOLIC. If RUNAVG is within 25% of BASELINE, Trend returns.

The timer is then decremented and checked for a time out condition. If the timer has not yet timed out the routine then returns to read a next value of $V_{IN}$. Once the timer times out the program automatically returns to measure the subject's blood pressure and to reset the variables SYSTOLIC and DIASTOLIC in accordance with the measured values. At any time, a new measurement of blood pressure, a new setting of SYSTOLIC and DIASTOLIC, and a new calculation of calibration factors M and B can be commanded with an appropriate key entry.

FIG. 16b is a detailed flow chart of the routine Pulseamp. The heart pulse waveform characteristically includes two minima and two maxima within each cycle. The routine Pulseamp first reads a value of the oximetric finger probe waveform from the A/D converter 30 and stores it in the variable ADDAT. The routine then cycles in the loop 100 to set the variable MAX1 equal to a first local maximum of ADDAT. Once a first local maximum is found in the loop 100, the routine then finds a first local minimum MIN1 in the loop 102. Then a second local maximum MIN2 is found in the loop 104 and a second local minimum MIN2 is found in the loop 106. Throughout operation of the loops 100-104, A/D measurements are output to the display 14 using the previously established calibration factors.

Once MAX1, MIN1, MAX2, and MIN2 have been set, the routine then sets the variable MIN equal to the smaller of MIN1 and MIN2 and sets the variable MAX equal to the larger of MAX1 and MAX2. The variable MINTOTAL is used to maintain a running total of each value of variable MIN, and the variable MAXTOTAL is used to maintain a running total of the variable MAX. Thus, in each pulse cycle of the waveform generated by the oximetric finger probe 18, the routine of Figure 16b finds the maximum value and the minimum value of the waveform, and sums these maximum and minimum values in appropriate variables. For example, when the counter is initially set equal to 5, MAXTOTAL will include the sum of five consecutive maximum values of respective pulse cycles and MINTOTAL will contain the sum of the corresponding five minimum values of the pulse waveform.

At this point the average amplitude AMP is calculated as (MAXTOTAL−MINTOTAL)/TOTAL, where TOTAL is the initial value of the counter. The routine Pulseamp then returns.

FIG. 16c shows a flow chart of the routine Rescale, which updates the running ten minute average of M and then sets M and B according to the following formulas:

$$M = \frac{SYSTOLIC - DIASTOLIC}{AMP}$$

$$B = DIASTOLIC - M \cdot \frac{MINTOTAL}{TOTAL}$$

The routine Check is then called and then the routine Rescale returns.

FIG. 16e shows a flow chart of the routine Check. This routine first checks to determine whether the trend in the calibration factor M indicates a vascular bed constriction. M correlates core blood pressures as measured with the blood pressure cuff 34 with blood flow at an extremity as measured by the oximetric finger probe 18. In general, M will vary, both from subject to subject and over time for a given subject. The first type of variation is a result of differences in finger opacity, skin pigmentation, and the like from subject to subject. The second type of variation relates to variations in blood volume and blood flow characteristics at the finger monitored by the oximetric finger probe 18. For example, when the vascular bed of the finger being monitored by the finger probe 18 constricts, the value of M will rise. Thus, by monitoring the changes in M over time, excessive increases in M can be taken as an indication of vascular bed constriction and an appropriate warning message displayed. In the example of FIG. 16e, an increase in M by more than 25% as compared with the average value of M over the last ten minutes is taken as an indication of significant vascular bed constriction.

Conversely, if the vascular bed of the finger dilates, the amplitude of the waveform generated by the oximetric finger probe 18 will increase, causing a reduction in the value of M. In the example of FIG. 16e a decrease in M by more than 25% as compared with the average value of M over the last ten minutes is taken as an indication of significant vascular bed dilation and an appropriate warning message displayed.

In alternate embodiments the approach used to detect significant trends in M may be varied, as can the thresholds and time periods described above.

The routine Check also compares the measured blood pressure with stored limits and displays appropriate warning messages if these limits are exceeded. Similarly, the routine Check monitors the regularity of the heart beat as indicated by the waveform generated by the oximetric finger probe 18 and displays an appropriate warning message if an irregular heart beat is detected.

The system described above provides an early warning of excessive dilation or constriction of the vascular bed at the finger. As explained above, a decrease in pulse amplitude as measured at the fingertip which does not correspond to a decrease in core blood pressure as measured with the occluding cuff indicates a constriction in the vascular bed at the fingertip. This may provide an warning of a potential drop in core blood pressure such as circulatory failure or shock. Similarly, an increase in pulse amplitude from the finger probe which does not correspond to an increase in core blood pressure as measured with the blood pressure cuff indicates a dilation of the vascular bed at the fingertip. This indication may precede an actual increase in core blood pressure and so may warn of such a possibility. Furthermore, the calibrated waveform display of this invention provides a number of important advantages. Because the waveform is automatically calibrated on a periodic basis, the displayed waveform provides both waveform information regarding the shape of the pulse waveform and core blood pressure values for the waveform. Such a calibrated waveform is of considerable diagnostic value, and in the system described above is obtained without increasing the hardware of the monitor 10 and without requiring any sort of invasive blood pressure measurements.

The use of the oximetric finger probe 18 provides important advantages in that it does not increase the hardware requirements of the system. The oximeter may be positioned on any suitable part of the skin of the subject, such as the finger described above or the forehead. (Of course, such repositioning of the oximeter may affect the way in which the oximeter signal is processed to monitor vasomotor activity.) However, other sources of a pulse waveform can be used with this invention, including waveforms generated from occluding cuffs, from strain gauges, and from oscillometric or impedance measurements. Similarly, a variety of techniques can be used to measure the blood pressure of the subject, including oscillometric techniques and techniques based on measuring the Korotkoff sounds. In some applications where it is of key importance to provide advance warning of drops or rises in core blood pressure, invasive catheters with suitable pressure transducers can be used to measure the core blood pressure.

CONCLUSION

It should be apparent from the foregoing discussion that an improved vital signs monitor has been described which provides important advantages in terms of artifact rejection and improvements in accuracy with little or no increase in hardware complexity. This is accomplished in all of the monitoring techniques described above by cross-referencing data from multiple sensor channels in order to reduce artifacts and to improve measuring accuracy.

Of course, it should be understood that a wide range of changes and modifications can be made to the preferred embodiments described above. It is therefore intended that the foregoing detailed description be regarded as illustrative rather than limiting, and that it be understood that it is the following claims, including all equivalents, which are intended to define the scope of this invention.

We claim:

1. In a monitor of the type comprising an ECG signal channel and an oximeter signal channel, the improvement comprising:

means, responsive to the ECG signal channel, for generating a series of first pulses indicative of heart pulses of a subject as indicated by the ECG signal channel;

means, responsive to the oximeter signal channel, for generating a series of second pulses indicative of heart pulses of the subject as indicated by the oximeter signal channel;

means, responsive to both the first and second pulses, for identifying those pulses having more regularly repeating pulse intervals, said identifying means comprising:

means for storing a previous pulse rate measure;

means for determining a first pulse rate measure in response to the first pulses during a selected interval;

means for determining a second pulse rate measure in response to the second pulses during the selected interval; and means for selecting the one of the first and second pulse rate measures which is closer to the previous pulse rate measure; and means, responsive to the identified pulses, for generating a pulse rate signal indicative of pulse rate of the subject.

2. The invention of claim 1 wherein the identifying means comprises:
   means, operative when the first pulses are absent, for identifying consecutive ones of the second, pulses to the pulse rate signal generating means; and
   means, operative when the second pulses are absent, for identifying consecutive ones of the first pulses to the pulse rate signal generating means.

3. In a monitor of the type comprising first and second heart pulse sensors, the improvement comprising:
   means, responsive to the first heart pulse sensor, for generating a series of first pulses indicative of heart pulses of a subject;
   means, responsive to the second heart pulse sensor, for generating a series of second pulses indicative of heart pulses of the subject;
   means, responsive to both the first and second pulses, for identifying selected pulses having regularly repeating pulse intervals, said identifying means comprising:
      means for storing a previous pulse rate measure;
      means for determining a first pulse rate measure in response to the first pulse during a selected interval;
      means for determining a second pulse rate measure in response to the second pulses during the selected interval; and
      means for selecting the one of the first and second pulse rate measures which is closer to the previous pulse rate measure; and
   means, responsive to the identified pulses, for generating a pulse rate signal indicative of pulse rate of the subject.

4. The invention of claim 3 wherein the identifying means comprises:
   means, operative when the first pulses are absent, for identifying consecutive ones of the second, pulses to the pulse rate signal generating means; and
   means, operative when the second pulses are absent, for identifying consecutive ones of the first pulses to the pulse rate signal generating means.

* * * * *